(12) United States Patent
Jung et al.

(10) Patent No.: US 12,012,387 B2
(45) Date of Patent: Jun. 18, 2024

(54) TRIAZINE COMPOUND AND USE THEREOF

(71) Applicant: Ha Yun Jung, Wonju-si (KR)

(72) Inventors: Ha Yun Jung, Wonju-si (KR); Jeong Kyu Bang, Cheongju-si (KR); Pethiah Gunasekaran, Cheongju-si (KR); Ji Eun Lee, Sejong-si (KR)

(73) Assignee: Ha Yun Jung, Wonju-si (KR)

( * ) Notice: Subject to any disclaimer, the term of this patent is extended or adjusted under 35 U.S.C. 154(b) by 559 days.

(21) Appl. No.: 17/041,362

(22) PCT Filed: Mar. 25, 2019

(86) PCT No.: PCT/KR2019/003419
§ 371 (c)(1),
(2) Date: Sep. 24, 2020

(87) PCT Pub. No.: WO2019/190131
PCT Pub. Date: Oct. 3, 2019

(65) Prior Publication Data
US 2021/0078961 A1 Mar. 18, 2021

(30) Foreign Application Priority Data
Mar. 30, 2018 (KR) ........................ 10-2018-0036966

(51) Int. Cl.
*A61K 8/04* (2006.01)
*A61K 8/49* (2006.01)
(Continued)

(52) U.S. Cl.
CPC ............ *C07D 251/50* (2013.01); *A61K 8/042* (2013.01); *A61K 8/4966* (2013.01); *A61K 9/06* (2013.01);
(Continued)

(58) Field of Classification Search
CPC ... C07C 231/02; C07C 235/38; C07C 209/60; C07C 213/00; C07C 213/02; C07C 217/28; C07C 217/42; C07C 231/04; C07C 235/34; C07C 323/63; C07C 67/11; C07C 69/653; C07C 279/28; C07C 309/17; A61P 1/00; A61P 29/00; A61P 37/06; A61P 1/04; A61P 1/16; A61P 1/18; A61P 11/00; A61P 11/02; A61P 11/06; A61P 3/10; A61P 35/00; A61P 43/00; A61P 15/00; A61P 19/02; A61P 19/10; A61P 25/00; A61P 25/04; A61P 25/24; A61P 29/02; A61P 3/04; A61P 31/18; A61P 37/02; A61P 7/00; A61P 3/08; A61P 37/00; A61P 37/04; A61P 31/12; A61P 9/10; A61P 33/02; A61P 9/00; A61P 17/06; A61P 25/28; A61P 37/08; A61P 3/00; A61P 9/12; A61P 13/12; A61P 19/00; A61P 24/04; A61P 35/02; A61P 9/04; A61P 25/16; A61P 27/02; A61P 21/00; A61P 5/00; A61P 7/06; A61P 19/08; A61P 35/04; A61P 13/00; A61P 25/08; A61P 25/20; A61P 7/10; A61P 13/02; A61P 17/02; A61P 31/00; A61P 7/02; A61P 1/10; A61P 31/04; A61P 33/06; A61P 5/50; A61P 13/10; A61P 25/06; A61P 25/22; A61P 33/00; A61P 1/02; A61P 1/12; A61P 11/08; A61P 11/16; A61P 17/04; A61P 19/06; A61P 21/02; A61P 25/18; A61P 25/26; A61P 25/30; A61P 27/06; A61P 27/10; A61P 27/16; A61P 31/06; A61P 31/10; A61P 9/02; A61P 9/08; A61P 1/08; A61P 11/14; A61P 15/02; A61P 19/04; A61P 21/04; A61P 25/34; A61P 31/02; A61P 31/16; A61P 9/14; C07F 7/1804; C07F 7/0838; A61K 31/53; A61K 45/06; A61K 33/26; A61K 47/02; A61K 9/10; A61K 31/4196; A61K 8/04; A61K 31/506; A61K 9/0019; A61K 31/7135; A61K 31/437; A61K 8/4966; A61K 2300/00; A61K 31/295; A61K 31/497; A61K 31/5025; A61K 31/52; A61K 31/538; A61K 31/721; A61K 36/515; A61K 47/10; A61K 47/186; A61K 47/20; A61K 47/24;
(Continued)

(56) References Cited

U.S. PATENT DOCUMENTS

2006/0194803 A1   8/2006   Kubota et al.
2009/0291079 A1   11/2009   Venkatesan et al.

FOREIGN PATENT DOCUMENTS

CN   107235925 A   * 10/2017   ............. A61K 31/53
CN   107235925 A   10/2017
(Continued)

OTHER PUBLICATIONS

CN107235925A translation; Ma Mingming, Zhang Ning, Yan Ziquiang. (Year: 2017).*

*Primary Examiner* — Audrea B Coniglio
*Assistant Examiner* — Audrea Buckley
(74) *Attorney, Agent, or Firm* — Revolution IP, PLLC

(57) ABSTRACT

The present invention relates to a triazine compound and a use thereof. Specifically, the amphipathic triazine compound according to the present invention has a strong anti-bacterial effect and anti-inflammatory effect, while being excellently effective for preventing, alleviating, or treating an allergy. Also, the triazine compound according to the present invention is expected to be usefully utilized as a compound for external application on the skin, which is not toxic and can be safely used on the skin.

4 Claims, 6 Drawing Sheets

(51) Int. Cl.
    *A61K 9/06*     (2006.01)
    *A61K 9/12*     (2006.01)
    *A61K 9/70*     (2006.01)
    *C07D 251/50*     (2006.01)
    *C07D 251/54*     (2006.01)

(52) U.S. Cl.
    CPC ............... *A61K 9/12* (2013.01); *A61K 9/7023* (2013.01); *C07D 251/54* (2013.01)

(58) Field of Classification Search
CPC ........ A61K 47/26; A61K 47/30; A61K 47/32; A61K 2236/33; A61K 31/541; A61K 31/553; A61K 36/258; A61K 47/58; A61K 2236/51; A61K 31/34; A61K 31/519; A61K 31/7048; A61K 36/47; A61K 36/48; A61K 8/042; A61K 9/06; A61K 9/12; A61K 9/7023; A61K 2236/331; A61K 2800/592; A61K 2800/82; A61K 31/00; A61K 31/165; A61K 31/381; A61K 31/444; A61K 35/36; A61K 36/185; A61K 36/234; A61K 36/236; A61K 36/486; A61K 36/489; A61K 36/51; A61K 36/605; A61K 36/714; A61K 36/725; A61K 36/756; A61K 36/83; A61K 36/904; A61K 8/064; A61K 8/27; A61K 8/35; A61K 8/37; A61K 8/602; A61K 8/63; A61K 8/9783; A61K 2236/39; A61K 31/10; A61K 31/133; A61K 31/18; A61K 31/4164; A61K 31/4178; A61K 31/433; A61K 31/4409; A61K 31/4745; A61K 31/4965; A61K 31/505; A61K 31/522; A61K 31/5355; A61K 31/5386; A61K 31/57; A61K 31/58; A61K 31/60; A61K 31/63; A61K 35/12; A61K 35/35; A61K 35/413; A61K 36/11; A61K 36/15; A61K 36/21; A61K 36/232; A61K 36/233; A61K 36/238; A61K 36/25; A61K 36/254; A61K 36/264; A61K 36/28; A61K 36/282; A61K 36/285; A61K 36/286; A61K 36/296; A61K 36/324; A61K 36/328; A61K 36/355; A61K 36/488; A61K 36/53; A61K 36/535; A61K 36/54; A61K 36/56; A61K 36/59; A61K 36/61; A61K 36/65; A61K 36/71; A61K 36/716; A61K 36/732; A61K 36/758; A61K 36/85; A61K 36/8945; A61K 36/8967; A61K 36/899; A61K 36/9066; A61K 38/13; A61K 38/446; A61K 8/25; A61K 8/411; A61K 8/466; A61K 8/49; A61K 8/4906; A61K 8/4913; A61K 8/492; A61K 8/4926; A61K 8/494; A61K 8/4953; A61K 8/585; A61K 8/70; A61K 8/894; A61K 9/0014

See application file for complete search history.

(56) References Cited

FOREIGN PATENT DOCUMENTS

| | | |
|---|---|---|
| EP | 0545149 A1 | 6/1993 |
| JP | H05-262749 A | 10/1993 |
| KR | 10-2006-0030922 A | 4/2006 |
| KR | 10-2011-0002485 A | 1/2011 |
| KR | 10-2012-0011664 A | 2/2012 |

* cited by examiner

TRIAZINE COMPOUND AND USE THEREOF

TECHNICAL FIELD

The present invention relates to a novel triazine compound and a use thereof. Particularly, the present invention relates to a novel triazine compound or a salt thereof and a composition for anti-inflammatory use, for antibacterial use, or for preventing, alleviating or treating allergic diseases, comprising the novel triazine compound or the salt thereof.

BACKGROUND ART

Antimicrobial peptides (AMP) are known to be part of innate immunity, which most organisms use to protect themselves from external dangers such as infection. The AMPs are widely present throughout living things such as animals and plants, including insects and even some microorganisms, and their existence was first identified in the skin mucus of frogs in the 1960s, and now thousands of the AMPs have been discovered, synthesized and studied in various species.

Out of the AMPs, cationic antimicrobial peptides have drawn attention as a new antibiotic that treats drug-resistant pathogens due to a unique mode of action and a rapid death rate. The cationic antimicrobial peptides exist in the form of helix ($\alpha$-helix) and beta sheet ($\beta$-sheet), and form an amphiphilic structure by introducing a cationic group on one side and a hydrophobic group on the other side.

In general, the cationic antimicrobial peptides are usually composed of about 20 amino acids, many of which are composed of amino acids having positive charges such as lysine, arginine, histidine, etc. Cationicity caused by the positively charged amino acids plays an important role in an interaction with an outer membrane or a cytoplasmic membrane of bacteria. In addition, hydrophobicity caused by the introduction of a hydrophobic group enables a hydrophobic helix core portion of peptides to make a stable attachment through a hydrophobic interaction with membrane lipid acyl chains. In other words, amphipathicity, which has both cationic and hydrophobic properties, plays an important role in an initial interaction between peptide and bacterial cell membrane. In particular, since gram-negative bacteria have lipopolysaccharide (LPS) on cell walls, it is known that cationic antimicrobial peptides adhere thereto, so as to increase the permeability of the membrane, thereby exhibiting an effective antibacterial action. However, it has been also reported that variants without a hydrophobic group show less activity to the gram-negative bacteria. In contrast, the cationic antimicrobial peptides have a complicated structure and thus require high costs in synthesis and study on structure activity relationship (SAR), and have serious disadvantages such as a hemolytic action (destruction of red blood cells).

As an alternative to solve the problems of cationic antimicrobial peptides, the present inventors have repeatedly studied an amphiphilic low-molecular compound containing a cationic group and a hydrophobic group. As a result, the present inventors have devised a triazine compound having not only a controlled hemolytic action, but also high antibacterial activity by introducing a cationic group and a hydrophobic residue including amine or guanidine into a scaffold of triazine. Furthermore, the present invention has been completed by confirming that the triazine compound according to the present invention has an anti-inflammatory effect and also exerts an excellent effect on allergic diseases.

DISCLOSURE

Technical Problem

An object of the present invention is to provide a novel triazine compound which is excellent in biostability and antibacterial activity and thus can be used as a novel antibiotic.

Another object of the present invention is to provide a cosmetic composition containing the triazine compound or the salt thereof as an effective ingredient, and having excellent anti-inflammatory and antibacterial effects.

Another object of the present invention is to provide a cosmetic composition containing the triazine compound or the salt thereof as an effective ingredient, and having an excellent effect on preventing or alleviating allergic diseases.

Another object of the present invention is to provide a pharmaceutical composition containing the triazine compound or the salt thereof as an effective ingredient, and having an excellent effect on preventing or treating allergic diseases.

Technical Solution

In order to achieve the objects as described above, there may be provided a triazine compound represented by the following formula 1:

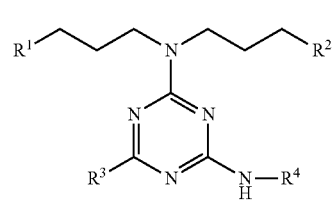

[Formula 1]

in the formula 1 above, $R^1$ and $R^2$ are each independently *—N($R^{11}$)($R^{12}$) or guanidine, and the $R^{11}$ and $R^{12}$ are each independently hydrogen or $C_1$-$C_{30}$ alkyl;

$R^3$ is halogen, $C_1$-$C_{30}$ alkylamino or $C_3$-$C_{30}$ cycloalkylamino;

$R^4$ is $C_1$-$C_{30}$ alkyl or $C_3$-$C_{30}$ cycloalkyl; and the alkylamino or cycloalkylamino of the $R^3$ and the alkyl or cycloalkyl of the $R^4$ are each independently further substituted with at least one substitute selected from $C_6$-$C_{30}$ aryl and $C_6$-$C_{30}$ heteroaryl, and the heteroaryl includes at least one selected from B, N, O, S, Se, —P(=O)—, —C(=O)—, Si and P.

There may be provided the triazine compound, wherein the $R^1$ and $R^2$ are each independently *—N($R^{11}$)($R^{12}$) or guanidine, and the $R^{11}$ and $R^{12}$ are each independently hydrogen or $C_1$-$C_7$ alkyl; the $R^3$ is halogen; and the $R^4$ is $C_1$-$C_{30}$ alkyl or $C_3$-$C_{30}$ cycloalkyl, and the alkyl or cycloalkyl of the $R^4$ is each independently further substituted with at least one substitute selected from $C_6$-$C_{30}$ aryl.

There may be provided the triazine compound represented by the following formula 2:

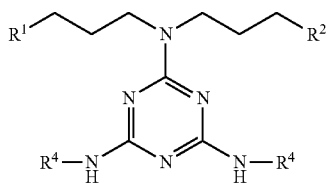

[Formula 2]

in the formula 2 above,

R$^1$ and R$^2$ are each independently *—N(R$^{11}$)(R$^{12}$) or guanidine, and the R$^{11}$ and R$^{12}$ are each independently hydrogen or C$_1$-C$_7$ alkyl; and R$^4$ is each independently C$_1$-C$_{30}$ alkyl or C$_3$-C$_{30}$ cycloalkyl, the alkyl or cycloalkyl of the R$^4$ is each independently further substituted with at least one substitute selected from C$_6$-C$_{30}$ aryl, and the R$^4$ are the same as or different from each other.

There may be provided the triazine compound, wherein the R$^1$ and R$^2$ are each independently *—NH$_2$ or guanidine; and the R$^4$ is C$_1$-C$_7$ alkyl or C$_3$-C$_7$ cycloalkyl, and the alkyl or cycloalkyl of the R$^4$ is each independently further substituted with at least one substitute selected from C$_6$-C$_{20}$ aryl.

There may be provided the triazine compound, wherein the R$^1$ and R$^2$ are each independently *—NH$_2$ or guanidine; and the R$^4$ is C$_{10}$-C$_{20}$ aryl-C$_1$-C$_7$ alkyl or C$_{10}$-C$_{20}$ aryl-C$_3$-C$_7$ cycloalkyl.

In order to achieve the objects as described above, there may be provided a cosmetic composition for anti-inflammatory use or for antibacterial use, containing the triazine compound represented by the formula 1 or the salt thereof.

In addition, there may be provided a cosmetic composition for preventing or alleviating allergic diseases, containing the triazine compound represented by the formula 1 or the salt thereof.

Furthermore, there may be provided a pharmaceutical composition for preventing or treating allergic diseases, containing the triazine compound represented by the formula 1 or the salt thereof.

The allergic diseases may be selected from allergic dermatitis, atopic dermatitis, contact dermatitis, hives, pruritus and the like.

The pharmaceutical composition may be formulated into a dosage form of lotion, ointment, gel, cream, patch, aerosol or the like.

Advantageous Effects

The amphipathic triazine compound according to the present invention implements a strong antibacterial effect and does not show toxicity in a range of activity thereof and thus can be very safe to the skin.

In addition, the amphipathic triazine compound according to the present invention implements an excellent anti-inflammatory effect. Specifically, the triazine compound can effectively inhibit cytokines and effectively control a degree of hemolytic action. In other words, according to the present invention, an excellent effect on preventing or alleviating various inflammatory diseases and allergic diseases may be provided.

In addition, the amphipathic triazine compound according to the present invention implements an excellent effect on preventing or treating inflammatory diseases accompanied by pruritus, or allergic diseases.

In short, according to the present invention, it was confirmed that it is possible to provide the amphiphilic triazine compound capable of implementing the above-described effects in a very economical manner and effectively controlling a hemolytic action, which was a problem of the conventional cationic antimicrobial peptide. Thus, according to the present invention, the amphiphilic triazine compound is provided as a novel pharmacological use, and thus is expected to be usefully utilized as a composition for external application on the skin, which can be safely used on the skin.

BEST MODE

Figure 1:
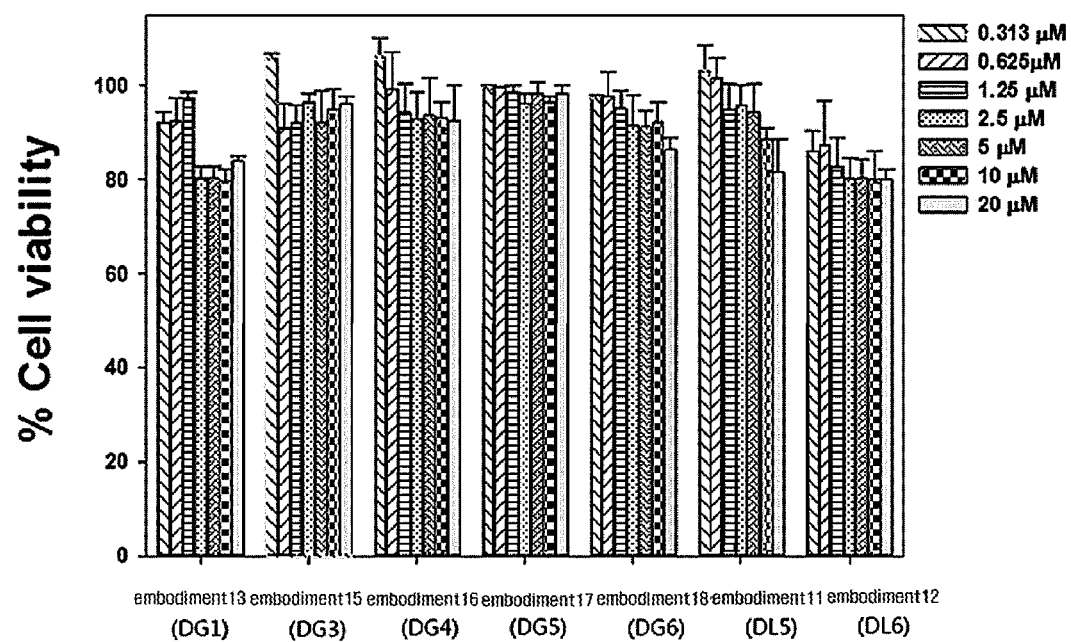
FIG. 1 is a view showing the results of identifying whether the triazine compound according to the present invention has toxicity to cells or not.

Hereinafter, the triazine compound according to the present invention and a use thereof will be described in detail. In this case, however, the technical and scientific terms used herein have the meanings conventionally understood by those skilled in the art to which the present invention pertains, unless otherwise defined. In addition, detailed descriptions of well-known functions or structures incorporated herein may be omitted when they make the subject matter rather unclear.

The term "alkyl" and substituents including alkyl used in the present specification may refer to organic radicals derived from straight-chain or branched-chain hydrocarbons.

In addition, the term "cycloalkyl" used in the present specification may refer to free radicals derived from fully saturated or partially unsaturated hydrocarbon rings of three to nine carbon atoms, including a case in which aryl or heteroaryl is fused therewith.

Furthermore, the term "alkylamino" used in the present specification may be represented by *—N(R$^a$)(R$^b$) and refer to free radicals including monoalkylamino or dialkylamino. In this case, the R$^a$ may be hydrogen or C$_1$-C$_{30}$ alkyl, and the R$^b$ may be C$_1$-C$_{30}$ alkyl.

Moreover, the term "cycloalkylamino" used in the present specification may be represented by *—N(R$^c$)(R$^d$) and refer to free radicals including monocycloalkylamino or dicycloalkylamino. In this case, the R$^c$ may be hydrogen or C$_3$-C$_{30}$ cycloalkyl, and the R$^b$ may be C$_3$-C$_{30}$ cycloalkyl.

In addition, the term "aryl-alkyl" used in the present specification may be represented by *-alkyl-aryl and refer to organic radicals in which aryl is substituted at the end of alkyl chain, and the aryl substituted at the end may be one or two.

Furthermore, the term "aryl-cycloalkyl" used in the present specification may be represented by *-cycloalkyl-aryl and refer to organic radicals in which aryl is substituted at the ring of cycloalkyl, and the aryl substituted may be one or two.

Moreover, the term "aryl" used in the present specification may refer to organic radicals derived from aromatic hydrocarbons by the removal of one hydrogen, and suitably include a single or fused ring system having four to seven ring atoms, preferably five or six ring atoms in each ring, and include even a form in which a plurality of aryls are linked by a single bond. Examples may include phenyl, naphthyl, biphenyl, terphenyl, anthryl, indenyl, fluorenyl, phenanthryl, triphenylenyl, pyrenyl, perylenyl, chrysenyl, naphthacenyl, fluoranthenyl, and the like, but are not limited thereto.

In addition, the term "heteroaryl" used in the present specification may refer to organic radicals derived from aromatic hydrocarbon by the removal of one hydrogen, and may be organic radicals derived from monocyclic or polycyclic aromatic hydrocarbon containing four to seven ring atoms having at least one selected from B, N, O, S, Se, —P(=O)—, —C(=O)—, Si, P and the like, suitably include four to seven ring atoms, preferably five or six ring atoms in each ring, and include even a form in which a plurality of aryls are linked by a single bond. Examples may include monocyclic heteroaryl such as furyl, thiophenyl, pyrrolyl, pyranyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc.; and polycyclic heteroaryl such as benzofuranyl, benzothiophenyl, isobenzofuranyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinolizinyl, quinoxalinyl, carbazolyl, phenanthridinyl, benzodioxolyl, etc., but are not limited thereto.

In addition, the term "halogen" used in the present specification may refer to an element of fluorine (F), chlorine (Cl), bromine (Br) or iodine (I).

Furthermore, the term "prevention" used in the present specification may refer to all the acts, which inhibit allergic diseases or delay a progress thereof by applying the composition of the present invention.

Moreover, the term "alleviation" used in the present specification may refer to all the acts, which alleviate or beneficially change allergic diseases by applying the composition of the present invention.

In addition, the term "treatment" used in the present specification may refer to all the acts, which inhibit, relieve or eliminate the development of allergic diseases by applying the composition of the present invention.

The present specification proposes a triazine compound having a low molecular weight without cytotoxicity, which solves the instability caused by a hemolytic action, which is a problem of the conventional cationic antimicrobial peptide, while exhibiting a wide range of antibacterial and anti-inflammatory activities.

The triazine compound may simulate the structural features of the cationic antimicrobial peptide. Specifically, the triazine compound may be an amphiphilic triazine compound including a cationic group and a hydrophobic group, and include at least two or more amine groups or guanidine groups. With those structural features, the triazine compound may properly control the balance of electric charges resulting from the hydrophobic group. In addition, the triazine compound may enhance antibacterial activity and anti-inflammatory activity by inducing an increase in hydrophobicity by the hydrophobic group.

Furthermore, the triazine compound may effectively inhibit the expression of cytokines, and exhibit an excellent effect on preventing, alleviating or treating allergic diseases. Specifically, the triazine compound may effectively inhibit tumor necrosis factor-α (TNF-α) and interleukin produced by macrophages among various cytokines. In addition, the triazine compound may have an excellent effect on inhibiting NO production.

Hereinafter, the triazine compound according to the present invention will be described in detail.

According to one embodiment of the present invention, there may be provided the triazine compound represented by the following formula 1:

[Formula 1]

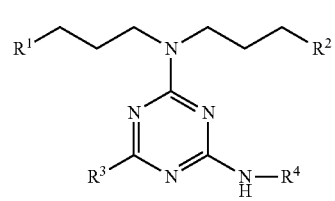

in the formula 1 above,
R$^1$ and R$^2$ are each independently *—N(R$^{11}$)(R$^{12}$) or guanidine, and the R$^{11}$ and R$^{12}$ are each independently hydrogen or C$_1$-C$_{30}$ alkyl; and
R$^3$ is halogen, C$_1$-C$_{30}$ alkylamino or C$_3$-C$_{30}$ cycloalkylamino;
R$^4$ is C$_1$-C$_{30}$ alkyl or C$_3$-C$_{30}$ cycloalkyl; and
the alkylamino or cycloalkylamino of the R$^3$ and the alkyl or cycloalkyl of the R$^4$ are each independently further substituted with at least one substitute selected from C$_6$-C$_{30}$ aryl and C$_6$-C$_{30}$ heteroaryl, and the heteroaryl includes at least one selected from B, N, O, S, Se, —P(=O)—, —C(=O)—, Si and P.

The triazine compound may have an amphiphilic structure (in which one side has a positively charged hydrophilic site and the other side has a hydrophobic site). With the above structural feature, the triazine compound may electrostatically interact with a negatively charged bacterial membrane to effectively bind to a bacterial membrane, while penetrating the bacterial membrane by a hydrophobic site so as to implement antibacterial activity.

In addition, the triazine compound may not cause a decrease in the antibacterial activity even in the presence of salt.

The triazine compound may induce an increase in hydrophobicity or a decrease in electric charges by controlling substituents at positions 4 and 6 of triazine scaffold. In other words, it is possible to appropriately control a desired antibacterial activity or anti-inflammatory activity by controlling the substituents at positions 4 and 6 of the triazine scaffold.

According to one embodiment of the present invention, there may be provided the triazine compound, wherein the R$^1$ and R$^2$ are each independently *—N(R$^{11}$)(R$^{12}$) or guanidine, and the R$^{11}$ and R$^{12}$ are each independently hydrogen or C$_1$-C$_7$ alkyl; the R$^3$ is halogen; and the R$^4$ is C$_1$-C$_{30}$ alkyl or $C_3$-$C_{30}$ cycloalkyl, and the alkyl or cycloalkyl of the $R^4$ is each independently further substituted with at least one substitute selected from $C_6$-$C_{30}$ aryl.

In addition, according to one embodiment of the present invention, there may be provided the triazine compound represented by the following formula 2:

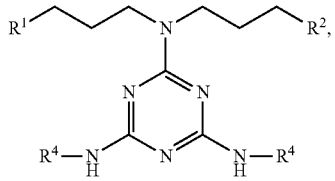

[Formula 2]

in the formula 2 above, $R^1$ and $R^2$ are each independently *—$N(R^{11})(R^{12})$ or guanidine, and the $R^{11}$ and $R^{12}$ are each independently hydrogen or $C_1$-$C_7$ alkyl; and $R^4$ is each independently $C_1$-$C_{30}$ alkyl or $C_3$-$C_{30}$ cycloalkyl, the alkyl or cycloalkyl of the $R^4$ is each independently further substituted with at least one substitute selected from $C_6$-$C_{30}$ aryl, and the $R^4$ are the same as or different from each other.

Specifically, it is preferable that the $R^1$ is hydrogen or $C_1$-$C_7$ alkyl and the $R^2$ is hydrogen in order to increase the cationicity of the triazine compound.

As one example, in the formula 1, it may be provided that the $R^1$ and $R^2$ are each independently *—$NH_2$ or guanidine; the $R^3$ is halogen; and the $R^4$ is $C_1$-$C_7$ alkyl or $C_3$-$C_7$ cycloalkyl, and the alkyl or cycloalkyl of the $R^4$ is each independently further substituted with at least one substitute selected from $C_6$-$C_{20}$ aryl.

As one example, in the formula 2, it may be provided that the $R^1$ and $R^2$ are each independently *—$NH_2$ or guanidine; and the $R^4$ is $C_1$-$C_7$ alkyl or $C_3$-$C_7$ cycloalkyl, and the alkyl or cycloalkyl of the $R^4$ is each independently further substituted with at least one substitute selected from $C_6$-$C_{20}$ aryl.

As one example, in the formula 2, it may be provided that the $R^1$ and $R^2$ are each independently *—$NH_2$ or guanidine; and the $R^4$ is $C_{10}$-$C_{20}$ aryl-$C_1$-$C_7$ alkyl or $C_{10}$-$C_{20}$ aryl-$C_3$-$C_7$ cycloalkyl.

As one example, in the formula 2, it may be provided that the $R^1$ and $R^2$ are each independently *—$NH_2$ or guanidine; and the $R^4$ is $C_{10}$-$C_{12}$ aryl-$C_1$-$C_4$ alkyl.

More specifically, the triazine compound may be at least one selected from the following structures:

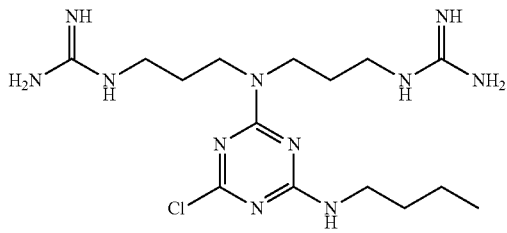

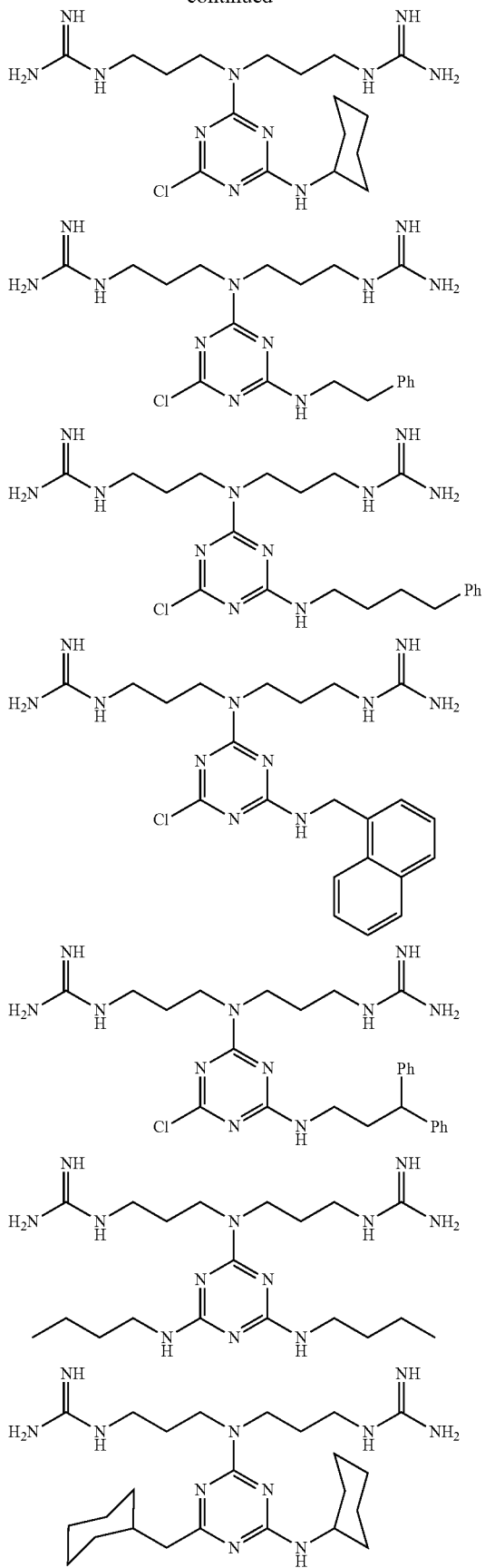

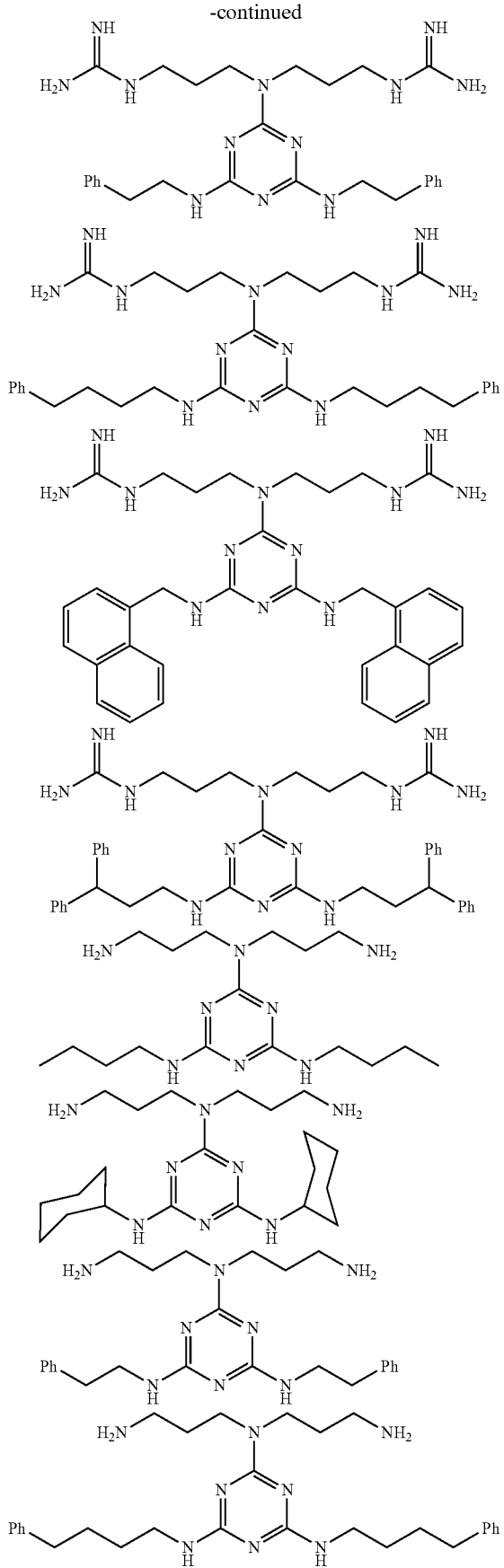

The triazine compound can effectively control the hemolytic action and also optimally inhibit the hemolytic action by controlling the structural features of amphiphilic properties. In addition, the triazine compound is a compound having a low molecular weight, easy to be mass-produced, and has excellent stability, and thus can be easily applied to commercialization.

Furthermore, the triazine compound has high stability against proteases, and thus antibacterial activity does not decrease even after protease treatment. In other words, according to the present invention, it is possible to solve the problems of developing an antibacterial agent caused by the instability of the conventional cationic antimicrobial peptide.

In addition, the triazine compound does not cause cytotoxicity while exhibiting broad antibacterial activity against both gram-positive bacteria and gram-negative bacteria. In other words, the triazine compound may be safely used even in a high concentration.

In addition, the triazine compound may show excellent anti-inflammatory activity by effectively inhibiting the production of nitrite (nitric oxide, NO) and cytokines such as TNF-α in cells stimulated by lipopolysaccharide (LPS).

Furthermore, the triazine compound may effectively inhibit TNF-α, IL-6 and the like, produced by macrophages among various cytokines, and thus exhibit an excellent effect on skin diseases accompanied by inflammation or pruritus, or allergic diseases.

It is extremely exceptional for the conventional antibacterial agent to exhibit antibacterial activity while showing anti-inflammatory activity at the same time. A novel pharmacological use of the amphiphilic triazine compound can be provided in a very economical way by controlling an inflammatory reaction, which is a side effect resulting from antibacterial treatment.

Hereinafter, the pharmacological use of the triazine compound according to the present invention will be described in detail.

According to one embodiment of the present invention, a pharmacological use may be a cosmetic composition having an anti-inflammatory or antibacterial effect or being excellent in preventing or alleviating allergic diseases.

Specifically, the cosmetic composition according to the present invention may contain the triazine compound represented by the formula 1 or the salt thereof as an effective ingredient, and specific uses thereof are as follows.

As one example, the cosmetic composition may be a cosmetic composition for anti-inflammatory use.

As one example, the cosmetic composition may be a cosmetic composition for antibacterial use.

As one example, the cosmetic composition may be a cosmetic composition for preventing or alleviating allergic diseases.

The cosmetic composition according to one embodiment of the present invention may contain 0.01 to 10 wt % of the triazine compound or the salt thereof, particularly 0.01 to 5 wt %, and more particularly 0.1 to 3 wt % of the triazine compound or the salt thereof based on the total weight of the composition. In this case, the remaining amount of the composition may be water.

In addition, the salt is a pharmaceutically acceptable salt and is not limited as long as the salt is an organic acid or an inorganic acid commonly used in the art.

Examples may include organic acids such as formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxy acetic acid, benzenesulfonic acid, p-toluenesulfonic acid, methanesulfonic acid-based salts, etc.; inorganic acids such as hydrochloric acid, bromic acid, sulfuric acid, phosphoric acid, nitric acid, carbonic acid, boric acid salts, etc.; and the like, but the present invention is not limited thereto.

In addition, the cosmetic composition according to one embodiment of the present invention may be formulated into a dosage form such as a general emulsified formulation, a solubilized formulation and the like by using a conventionally known preparation method.

As one example, the cosmetic composition may be formulated into a dosage form selected from the group consisting of softening lotion, astringent lotion, nutritional lotion, eye cream, nourishing cream, massage cream, cleansing cream, cleansing foam, cleansing water, powder, essence, pack, etc.

In addition, the cosmetic composition may further contain additional additives as appropriate, depending on purposes. As one example, the additives may include at least one aqueous additive selected from stabilizers, emulsifiers, thickeners, humectants, liquid crystal film reinforcing agents, pH adjusting agents, antibacterial agents, water-soluble polymers, coating agents, metal ion sequestering agents, amino acids, organic amines, polymer emulsions, pH adjusters, skin nutrients, antioxidants, antioxidant aids, preservatives, fragrances, etc.; at least one oily additive selected from fats and oils, waxes, hydrocarbon oils, higher fatty acid oils, higher alcohols, synthetic ester oils, silicon oils, etc.; and the like.

In this case, each of the additives may be contained in an amount of 0.001 to 20 wt %, particularly 0.01 to 10 wt % and 0.05 to 10 wt % with regard to the total weight of the composition, but is not limited thereto.

Another pharmacological use according to one embodiment of the present invention may be a pharmaceutical composition having an anti-inflammatory and antibacterial effect, or being excellent in preventing or treating allergic diseases.

Specifically, the pharmaceutical composition according to the present invention may contain the triazine compound represented by the formula 1 or the salt thereof as an effective ingredient, and specific uses thereof are as follows.

As one example, the pharmaceutical composition may be a pharmaceutical composition for anti-inflammatory use.

As one example, the pharmaceutical composition may be a pharmaceutical composition for antibacterial use.

As one example, the pharmaceutical composition may be a pharmaceutical composition for preventing or treating allergic diseases.

In addition, the pharmaceutical composition according to one embodiment of the present invention may be formulated into a composition for external application on the skin, containing a pharmaceutically acceptable carrier, by using a commonly known preparation method.

As one example, the pharmaceutical composition may be formulated into a dosage form selected from the group consisting of lotion, ointment, gel, cream, patch, aerosol, etc.

In addition, the pharmaceutical composition may contain an additional pharmaceutically acceptable carrier as appropriate, depending on purposes. Examples may include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methyl hydroxybenzoate, propylhydroxybenzoate, talc, magnesium stearate or mineral oil, but is not limited thereto. In addition, the pharmaceutical composition may further contain lubricant, humectant, a sweetening agent, a flavoring agent, emulsifier, a suspending agent, preservative or the like, in addition to the above carriers.

In this case, each of the carriers may be contained in an amount of 0.001 to 20 wt %, particularly 0.01 to 10 wt %, and 0.05 to 10 wt % with regard to the total weight of the composition, but are not limited thereto.

The allergic diseases may be selected from allergic dermatitis, atopic dermatitis, contact dermatitis, hives, pruritus and the like.

Specifically, the pharmaceutical composition may be used for preventing or treating atopic dermatitis.

In addition, the pharmaceutical composition according to one embodiment of the present invention exhibits an excellent effect on all allergic diseases, skin diseases accompanied by pruritus, or the like, which correspond to prevention or treatment by the implementation of the effects according to the present invention described above, and is also expected to exert an excellent effect on inflammatory diseases caused by allergies.

Hereinafter, the present invention will be described in more detail through embodiments.

Prior to this, terms and words used in the present specification and the claims shall not be interpreted as commonly-used or dictionary meanings, but shall be interpreted as meanings and concepts relevant to the technical idea of the present invention based on a principle that the inventor may appropriately define the concept of the term to explain his/her invention in the best way. Therefore, the embodiments disclosed in the specification and the configurations depicted in the drawings are only the most preferred embodiments of the present invention, and do not represent all of the technical ideas of the present invention, so it should be understood that various equivalents and modifications may be substituted for the embodiments and the configurations at the time of filing of the present application.

Except as otherwise specified, the synthesis of all compounds was carried out by using standard Schlenk or glove box in nitrogen atmosphere, and the organic solvent used in a reaction was refluxed in sodium metal and benzophenone to remove moisture therefrom, and then distilled and degassed immediately before use. In addition, the glass utensils to be used were heated in an oven at 130° C. for one day to make them dry before being put into the glove box. $^1$H-NMR and $^{13}$C-NMR analysis of synthesized compounds was performed at room temperature by using Brucker DRX-400, and mass spectrometry was carried out by using a Shimadzu (MALDI-TOF) mass spectrometer.

(Evaluation Method)

1. Confirmation of Cytotoxicity

To confirm cytotoxicity, the cell viability (%) measured by the following method was calculated. Specifically, mouse macrophages (RAW264.7 cells, purchased from American Type Culture Collection) were incubated in DMEM medium (HyClone), to which 10% fetal bovine serum (FBS, HyClone) and antibiotics (100 units/mL of penicillin, 100 μg/mL of streptomycin and 25 μg/mL of amphotericin B) were added, at 37° C. in a humidified atmosphere containing 5% CO$_2$. Subculture was performed every two to three days, and the cells were separated by trypsin treatment and observed under an inverted microscope.

Cytotoxicity to mouse macrophages was measured by slightly modifying the MTT assay (*CancerRes.* 48, 4827-4833, 1988). Mouse macrophages were inoculated so that 2×10$^4$ cells may be contained in each well of a 96-well plate containing 150 μl of DMEM with 10% FBS added, and incubated for 24 hours at 37° C. in a humidified atmosphere containing 5% CO$_2$. After incubation, 20 μl of a solution of the triazine compound of the following example (used by sequentially diluting in DMCM medium by doubles) was added to each well, and further incubated for two days. Then, 20 μl of MTT (2,5-diphenyl-2H-tetrazolium bromide, Sigma) solution was added to each well at a concentration of 5 mg/mL, and further incubated at 37° C. for four hours. The precipitated MTT formazan was dissolved in 40 μl of 20% (w/v) SDS solution containing 0.01M HCl. The absorbance was measured at 570 nm by using a microplate ELISA reader (Molecular Devices, Sunnyvale, CA), and the cell viability (%) was shown in FIG. 1 below by using the following Equation 1.

Cell viability (%)=(Absorbance-*A*)/(Absorbance-*B*)× 100 [Equation 1]

[In Equation 1, Absorbance-A represents the absorbance of the reaction solution treated with each triazine compound measured at a wavelength of 570 nm; and Absorbance-B represents the absorbance of the solution not treated with the triazine compound measured at a wavelength of 570 nm.]

2. Confirmation of Hemolytic Action

To confirm the hemolytic action, the erythrocyte hemolytic activity (%) measured by the following method was calculated. Specifically, human red blood cells were diluted in physiological saline solution (PBS, pH 7.4) to a concentration of 8%, and each of the triazine compounds of the following example was treated at a concentration of 0 to 300 μM/well, so as to be reacted at 37° C. for one hour. Then, an amount of hemoglobin contained in the supernatant obtained by centrifugation at 1,000×g was identified by measuring the absorbance at a wavelength of 414 nm. As a reference for the degree of cell destruction, a control group was treated with 1% Triton X-100 (Sigma, USA) and reacted at 37° C. for one hour, after which the absorbance of the obtained supernatant was measured. Taking the erythrocyte hemolytic activity of Triton X-100 as a reference (100%), calculation was made by using the following equation 2.

Erythrocyte hemolytic activity (%)=(Absorbance *A*−Absorbance *B*)/(Absorbance *C*−Absorbance *B*)×100 [Equation 2]

[In Equation 2, Absorbance A represents the absorbance of the reaction solution treated with each triazine compound measured at a wavelength of 414 nm; Absorbance B represents the absorbance of the reaction solution treated with PBS measured at a wavelength of 414 nm; and Absorbance C represents the absorbance of the reaction solution treated with 1% Triton X-100 measured at a wavelength of 414 nm.]

3. Confirmation of Antibacterial Activity

To confirm the antibacterial activity, a minimal inhibitory concentration (MIC) value, which is a minimum concentration at which fungus bodies are not divided, was measured. Specifically, the strains disclosed in the following table 1 were purchased, incubated in each medium up to a mid-log phase, diluted to a fungus body concentration of 2×10$^5$ cells/100 μl, and inoculated into a micro titrate plate (Nunc, USA). Then, the triazine compound of the following example and melittin were respectively diluted in bovine serum albumin (BSA) solution by one-half from 96 wells, added to the plate, and incubated at 37° C. for 12 hours, after which the absorbance was measured at a wavelength of 600 nm by using a micro titrate plate reader (Merck Elisa reader, Germany) to determine an MIC value for each strain, and the results were shown in the table 1 below. A control group was treated with melittine by the same method as above, so as to determine an MIC value for each strain.

4. Confirmation of Stability Against Protease

To confirm the stability against the protease, trypsin degradation was identified by using a radial diffusion assay method after treatment with each of the triazine compounds of the following example. Specifically, the cultured strains (*Escherichia coli*) were incubated in 10 mL of LB medium at 37° C. for 18 hours, after which 10 μl of the culture fluid was inoculated into 10 mL of fresh BL medium and then further incubated for three hours, so as to obtain bacteria in a mid-logarithmic phase. For the radial diffusion assay method, a bacterial suspension (2×10$^6$ CFU/mL in LB) was mixed with 0.7% agarose and rapidly dispersed, after which the resulting mixed solution was poured into a 10 cm-long Petri dish. Each 5 μl of the triazine compound solution (10 mg/mL) of the following example was added to 25 μl of trypsin solution (0.2 μg/mL in PBS), and incubated at 37° C. for six hours. A reaction was terminated by freezing with liquid nitrogen, after which each 10 μl was taken, seeded on circular paper having a diameter of 6 mm placed on the Petri dish containing the agarose, and incubated overnight at 37° C. To quantify the inhibitory activity, the clearance zones of bacteria around the circular paper were measured to confirm the antibacterial activity. As a control group, melittine was used.

5-1. Confirmation of Anti-Inflammatory Activity

To confirm the anti-inflammatory activity, the RAW264.7 cell line (ATCC number: CRL-2278) was used to measure the inhibitory effect of nitrogen monoxide (NO) formation by the GRIESS method. Specifically, RAW264.7 cells, which are mouse macrophages, were subcultured several times, and the cultured cells were placed in a 24-well plate so that 3×10$^5$ cells were put into each well, and then incubated for 24 hours. Then, replacement was made with a cell medium containing each of the triazine compounds (100 μg/ml) of the following example. In this case, the cells were treated with 1 μg of lipopolysaccharide (LPS) as a stimulus and incubated for 24 hours. Each 100 μl of the supernatant was taken and transferred to a 96-well plate, after which each 100 μl of GRIESS solution was added and reacted at room temperature for ten minutes, so as to measure the absorbance at 540 nm.

5-2. Confirmation of Anti-Inflammatory Activity

To confirm the anti-inflammatory activity, the inhibitory effect on TNF-α production was measured. Specifically, RAW264.7 cells, which are the mouse macrophages cultured in a 24-well plate, were pre-treated with LPS (1 μg/mL) for one hour, after which each 100 μg/ml of the triazine compound of the following example was treated with 20 mM 5-ASA and 20 μM dexamethasone and incubated for 24 hours, and the resulting cell culture fluid was used. First, TNF-α capture antibodies were inserted into a 96-well ELISA plate and reacted overnight. The plate was washed six times with 1×PBS (PBS-T) containing 0.05% Tween-20, and then blocked for one hour at room temperature with 1× assay diluent solution containing 2% BSA. The plate was washed six times with 1×PBS-T, after which the cell culture fluid or TNF-α standard protein was added thereinto and reacted at room temperature for two hours. The resulting plate was again washed six times with 1×PBS-T, and the detection antibodies were inserted thereinto and reacted at room temperature for two hours. The plate was again washed six times with 1×PBS-T again, and avidin-HRP solution was added and reacted at room temperature for 30 minutes. The resulting plate was washed six times with 1×PBS-T solution, after which the TMB substrate solution was added and reacted at room temperature for final 30 minutes, and then a reaction stop solution (1M $H_3PO_4$) was added thereto to stop the reaction. With regard to the degree of reaction of the plate, the absorbance was measured at 450 nm with a microplate reader (TECAN, Gr, Austria). As a control, lipopolysaccharide (LPS) was used.

6. Confirmation of Atopic Dermatitis Alleviating Effect

To confirm an effect of alleviating atopic dermatitis, a three-week-old mouse was used by inducing atopic dermatitis in its ear from house dust mite extract (*Dermatophagoides farinae* extract, DFE) and DNCB (2,4-dinitrochlorobenzene). A lesion site was treated with each of the triazine compounds of the following example, and each lesion site was observed for 28 days.

Example 1

First Phase Derivatisation_MG Series

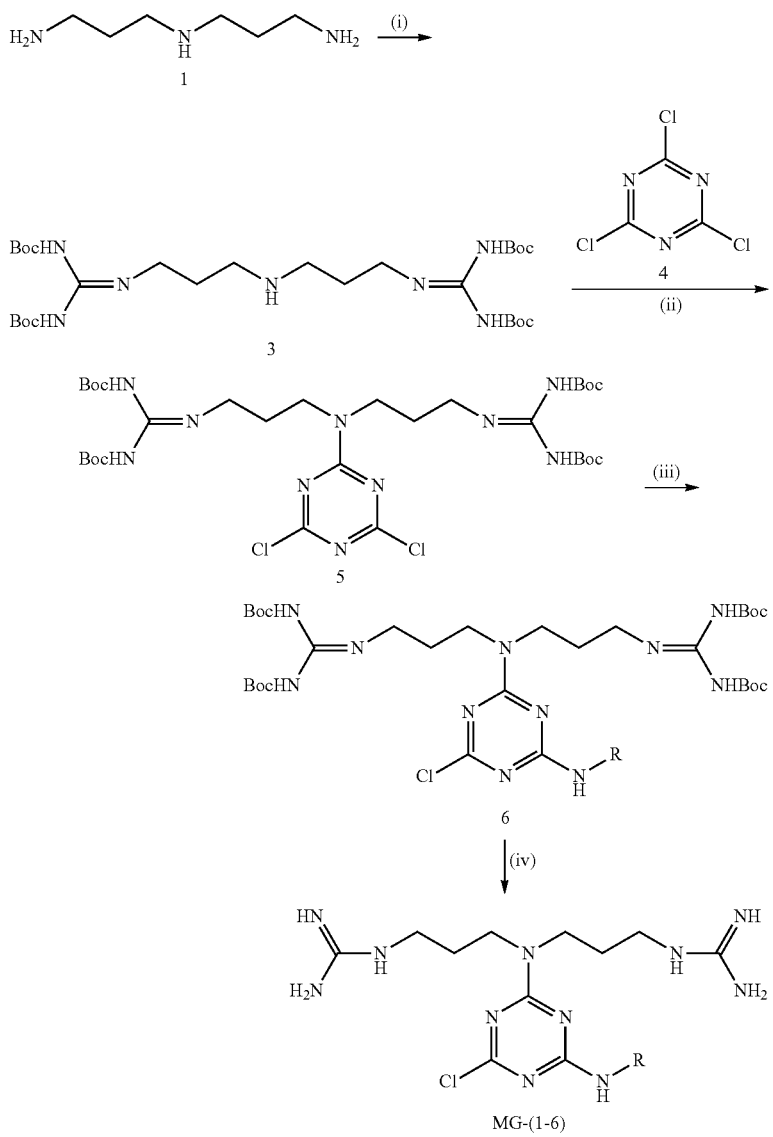

MG-(1-6)

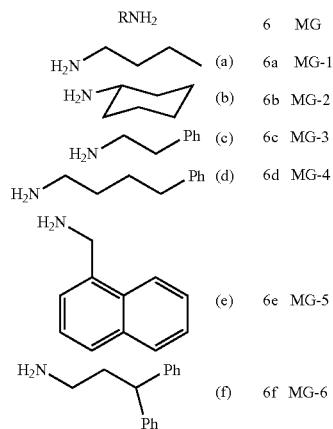

Step 1.

N,N'-di-boc-N-trifylguanidine 2 (4.27 g, 0.011 mol, 2.05 equiv.) dissolved in dichloromethane (30 mL) was slowly inputted into the solution (in DCM, 20 mL) in which nospermidine 1 (0.7 g, 0.005 mol, 2.05 equiv.) and triethylamine (3.0 mL, 0.021 mol, 4 equiv.) were dissolved, at 0° C. After that, the temperature was raised up to room temperature (23° C.) and reacted for six hours.

Water (30 mL) was inputted into the reaction solution to terminate the reaction, and an extraction was performed three times with dichloromethane. The extracted solution was dried, concentrated, and purified using column chromatography (DCM:MeOH:TEA=20:1:0.1) to obtain the compound 3 (2.25 g, 68%).

$^1$H NMR (400 MHz, CDCl$_3$) δ 11.49 (s, 2H), 8.56 (s, 2H), 3.51 (q, J=6.2 Hz, 4H), 2.67 (t, J=6.7 Hz, 4H), 1.77 (t, J=6.7 Hz, 4H), 1.49 (d, J=4.2 Hz, 36H). $^{13}$C NMR (100 MHz, CDCl$_3$) δ 163.6, 156.2, 153.1, 82.9, 79.1, 47.4, 39.2, 29.2, 28.3, 28.1. Maldi-tof m/z calcd for C$_{28}$H$_{53}$N$_7$O$_8$: 615.3, found 616.3 (M+H)$^+$ Step 2.

Cyanuric chloride 4 (0.89 g, 0.005 mol, 1.2 equiv.) and diisopropylethylamine (DIEA, 2.2 mL, 0.012 mol, 3 equiv.) dissolved in dichloromethane (20 mL) was slowly inputted into the solution (in DCM, 20 mL) in which the compound 3 (2.50 g, 0.004 mol, 1 equiv.) was dissolved, at 0° C. The reaction solution was reacted at the same temperature for three hours.

Water (30 mL) was inputted into the reaction solution to terminate the reaction, and then an extraction was performed twice with dichloromethane. The extracted solution was dried, concentrated, and purified using column chromatography (DCM:MeOH=98:2) to obtain the compound 5 (3 g, 97%).

$^1$H NMR (400 MHz, CDCl$_3$) δ 11.48 (s, 2H), 8.44 (s, 2H), 3.66 (t, J=7.1 Hz, 4H), 3.47 (q, J=6.4 Hz, 4H), 1.91 (p, J=6.9 Hz, 4H), 1.50 (d, J=2.4 Hz, 36H). $^{13}$C NMR (100 MHz, CDCl$_3$) δ 170.1, 164.9, 163.5, 156.2, 153.2, 83.2, 79.3, 45.3, 38.0, 28.3, 28.1, 26.9.

Step 3.

The n-butylamine (a) (24.2 mg, 0.330 mmol, 1.05 equiv.) dissolved in dichloromethane (10 mL) was slowly inputted into the solution (in DCM, 10 mL) in which the compound 5 (240 mg, 0.314 mmol, 1 equiv.) and diisopropylethylamine (DIEA, 0.11 mL, 0.628 mmol, 2 equiv.) were dissolved, at 0° C. After that, the temperature was raised up to room temperature (23° C.) and reacted for four hours.

Water (15 mL) was inputted into the reaction solution to terminate the reaction, and then an extraction was performed with dichloromethane (30 mL). The extracted solution was dried, concentrated, and purified using column chromatography (hexane:ethylacetate=4:1) to obtain the compound 6a (200 mg, 79%).

$^1$H NMR (500 MHz, CDCl$_3$) δ 12.02-11.36 (m, 2H), 8.95-7.99 (m, 2H), 6.41 (t, J=6.0 Hz, 1H), 3.55-3.65 (m, 4H), 3.52-3.46 (m, 2H), 3.42-3.36 (m, 4H), 1.96-1.86 (m, 2H), 1.80-1.75 (m, 2H), 1.68-1.61 (m, 2H), 1.53-1.51 (m, 36H), 1.46-1.36 (m, 2H), 1.32-1.23 (m, 2H), 0.94 (t, J=7.4 Hz, 3H).

Step 4.

The compound 6a was dissolved in an organic solvent (TFA:DCM (9:3 mL)), and reacted at room temperature for four hours.

The reaction solution was concentrated, after which cold diethyl ether was inputted thereinto, and the formed precipitate was separated by centrifugation. The precipitate was redissolved in acetonitrile, after which the solvent was removed therefrom to obtain MG-1 (17.6 mg, 44%).

$^1$H NMR (400 MHz, MeOD) δ 3.68-3.44 (m, 4H), 3.25 (d, J=7.2 Hz, 2H), 3.18-3.04 (m, 4H), 1.94-1.72 (m, 4H), 1.56-1.37 (m, 2H), 1.29 (p, J=7.4 Hz, 2H), 0.85 (t, J=7.3 Hz, 3H). 13C NMR (100 MHz, MeOD) δ 168.3, 165.2, 165.0, 160.9, 157.3, 44.5, 43.9, 40.2, 38.9, 38.4, 31.1, 26.8, 26.5, 19.7, 12.8. Maldi-tof m/z calcd for C$_{15}$H$_{30}$ClN$_{11}$: 399.2, found 400.1 (M+H)$^+$ Examples 2 to 6

MG-2 to MG-6 were prepared by a method similar to the preparation method of above Example 1.

The structural analysis data of the obtained 6b to 6f and MG-2 to MG-6 are shown in the table 1 below.

TABLE 1

| Compound | | Yield (%), $^1$H-NMR |
|---|---|---|
| Example 2 | 6b | (89 mg, 68%). $^1$H NMR (500 MHz, CDCl$_3$) δ 12.02-11.32 (m, 2H), 8.68-8.30 (m, 2H), 6.05-5.96 (m, 1H), 3.98-3.87 (m, 1H), 3.68-3.60 (m, 1H), 3.61-3.51 (m, 3H), 3.52-3.44 (m, 2H), 3.44-3.37 (m, 2H), 2.03-1.93 (m, 2H), 1.92-1.82 (m, 2H), 1.81-1.70 (m, 2H), 1.67-1.61 (m, 2H), 1.55-1.46 (m, 36H), 1.46-1.35 (m, 2H), 1.35-1.29 (m, 2H), 1.21-1.06 (m, 2H) |
| | MG-2 | (21.7 mg, 72%). $^1$H NMR (400 MHz, MeOD) δ 3.71-3.61 (m, 1H), 3.61-3.37 (m, 4H), 3.19-3.02 (m, 4H), 1.93-1.73 (m, 6H), 1.68 (d, J = 12.8 Hz, 2H), 1.55 (d, J = 12.8 Hz, 2H), 1.55 (d, J = 12.0 Hz, 1H), 1.35-1.07 (m, 5H). $^{13}$C NMR (100 MHz, MeOD) δ 169.2, 168.3, 164.9, 161.0, 157.3, 49.9, 49.4, 47.0, 44.7, 44.0, 38.4, 32.1, 26.7, 25.3, 24.7, 24.3. Maldi-tof m/z calcd for C$_{17}$H$_{32}$ClN$_{11}$: 425.2, found 426.1 (M + H)$^-$ |
| Example 3 | 6c | (220 mg, 66%). $^1$H NMR (500 MHz, CDCl$_3$) δ 11.71 (s, 1H), 11.51 (s, 1H), 8.69-8.39 (m, 2H), 7.34-7.29 (m, 1H), 7.28-7.18 (m, 2H), 7.18-7.14 (m, 2H), 6.55 (t, J = 6.4 Hz, 1H), 3.71-3.54 (m, 6H), 3.54-3.46 (m, 2H), 3.46-3.37 (m, 2H), 2.91-2.85 (m, 3H), 1.91-1.87 (m, 2H), 1.77-1.74 (m, 2H), 1.55-1.50 (m, 36H). |
| | MG-3 | (43 mg, 90%). $^1$H NMR (400 MHz, MeOD) δ 7.24-7.03 (m, 5H), 3.63-3.40 (m, 6H), 3.11 (q, J = 6.7 Hz, 4H), 2.85-2.71 (m, 2H), 1.90-1.70 (m, 4H). $^{13}$C NMR (100 MHz, MeOD) δ 169.2, 168.3, 164.8, 161.1, 157.3, 139.2, 128.5, 128.1, 126.0, 44.6, 44.0, 43.6, 42.0, 38.9, 38.4, 35.2, 26.5. Maldi-tof m/z calcd for C$_{19}$H$_{30}$ClN$_{11}$: 447.2, found 448.2 (M + H)$^-$ |
| Example 4 | 6d | (202 mg, 88%). $^1$H NMR (400 MHz, CDCl$_3$) δ 11.75 (s, 1H), 11.51 (s, 1H), 8.74-8.61 (m, 1H), 8.57-8.31 (m, 1H), 7.32-7.26 (m, 2H), 7.24-7.07 (m, 3H), 6.46 (t, J = 6.1 Hz, 1H), 3.66-3.51 (m, 4H), 3.51-3.35 (m, 6H), 2.65 (t, J = 7.3 Hz, 2H), 1.96-1.82 (m, 3H), 1.82-1.57 (m, 5H), 1.57-1.41 (m, 36H). |
| | MG-4 | (55 mg, 92%). $^1$H NMR (400 MHz, MeOD) δ 7.26 (t, J = 7.5 Hz, 2H), 7.22-7.10 (m, 3H), 3.77-3.55 (m, 4H), 3.39 (t, J = 6.5 Hz, 2H), 3.22 (t, J = 6.9 Hz, 4H), 2.66 (t, J = 7.2 Hz, 2H), 1.93 (dq, J = 14.6, 7.0 Hz, 4H), 1.75-1.55 (m, 4H). $^{13}$C NMR (100 MHz, MeOD) δ 169.2, 168.1, 164.8, 161.0, 157.3, 142.1, 128.0, 127.9, 125.4, 44.6, 44.0, 40.3, 38.9, 38.4, 35.2, 28.8, 28.4, 26.8, 26.5. Maldi-tof m/z calcd for C$_{21}$H$_{34}$ClN$_{11}$: 475.2, found 476.1 (M + H)$^-$ |
| Example 5 | 6e | (202 mg, 76%). $^1$H NMR (400 MHz, CDCl$_3$) δ 11.61 (s, 1H), 11.51 (s, 1H), 8.74 (t, J = 5.9 Hz, 1H), 8.51 (d, J = 6.2 Hz, 1H), 8.06-7.99 (m, 1H), 7.92-7.86 (m, 1H), 7.80 (t, J = 9.1 Hz, 1H), 7.57-7.49 (m, 2H), 7.49-7.39 (m, 2H), 6.71 (t, J = 5.8 Hz, 1H), 5.13 (d, J = 5.7 Hz, 2H), 3.67-3.55 (m, 4H), 3.50 (q, J = 6.7 Hz, 2H), 3.24 (q, J = 5.7 Hz, 1H), 3.34-3.24 (m, 1H), 1.91 (q, J = 6.9 Hz, 2H), 1.86-1.75 (m, 2H), 1.58-1.41 (m, 27H), 1.40 (s, 3H), 1.13 (s, 6H). $^{13}$C NMR (100 MHz, CDCl$_3$) δ 169.6, 166.1, 165.4, 165.4, 163.6, 156.2, 155.7, 153.3, 153.1, 144.3, 128.6, 128.5, 127.8, 127.7, 126.3, 83.2, 83.0, 79.3, 79.2, 48.8, 44.0, 42.9, 39.8, 38.2, 37.2, 35.5, 31.6, 29.7, 28.3, 28.1. |
| | MG-5 | (36 mg, 82%). $^1$H NMR (400 MHz, MeOD) δ 8.00 (d, J = 8.1 Hz, 1H), 7.86-7.77 (m, 1H), 7.76-7.66 (m, 1H), 7.52-7.29 (m, 4H), 4.92 (d, J = 3.1 Hz, 2H), 3.50 (q, J = 8.3, 7.1 Hz, 3H), 3.38 (t, J = 7.3 Hz, 1H), 3.08 (t, J = 6.8 Hz, 3H), 2.65 (t, J = 7.3 Hz, 1H), 1.77 (dq, J = 13.1, 6.5 Hz, 3H), 1.54 (p, J = 7.0 Hz, 1H). $^{13}$C NMR (100 MHz, MeOD) δ 168.6, 165.3, 164.9, 160.6, 157.3, 133.9, 131.1, 128.5, 127.5, 125.9, 125.5, 125.1, 124.4, 122.7, 117.8, 44.5, 44.0, 42.1, 38.4, 26.8, 26.2. Maldi-tof m/z calcd for C$_{22}$H$_{30}$ClN$_{11}$: 483.2, found 484.2 (M + H)$^-$ |
| Example 6 | 6f | (224 mg, 73%). $^1$H NMR (400 MHz, CDCl$_3$) δ 11.76 (s, 1H), 11.59-11.42 (m, 1H), 8.77-8.21 (m, 2H), 7.30-7.13 (m, 10H), 6.50 (t, J = 6.1 Hz, 1H), 3.99 (t, J = 7.7 Hz, 1H), 3.64-3.50 (m, 4H), 3.51-3.40 (m, 2H), 3.44-3.23 (m, 4H), 2.36 (q, J = 6.6 Hz, 2H), 1.86 (h, J = 6.4 Hz, 2H), 1.83-1.71 (m, 2H), 1.60-1.46 (m, 36H) |
| | MG-6 | (45 mg, 78%). $^1$H NMR (500 MHz, MeOD) δ 7.30-7.18 (m,1H), 4.12-4.02 (m, 1H), 3.69-3.53 (m, 4H), 3.12 (t, J = 7.1 Hz, 4H), 2.44-2.40 (m, 4H), 1.88 (t, J = 7.2 Hz, 4H). Maldi-tof m/z calcd for C$_{26}$H$_{36}$ClN$_{11}$: 537.3, found 538.3 (M + H)$^-$ |

Example 7

Second Phase Derivatisation_DL Series

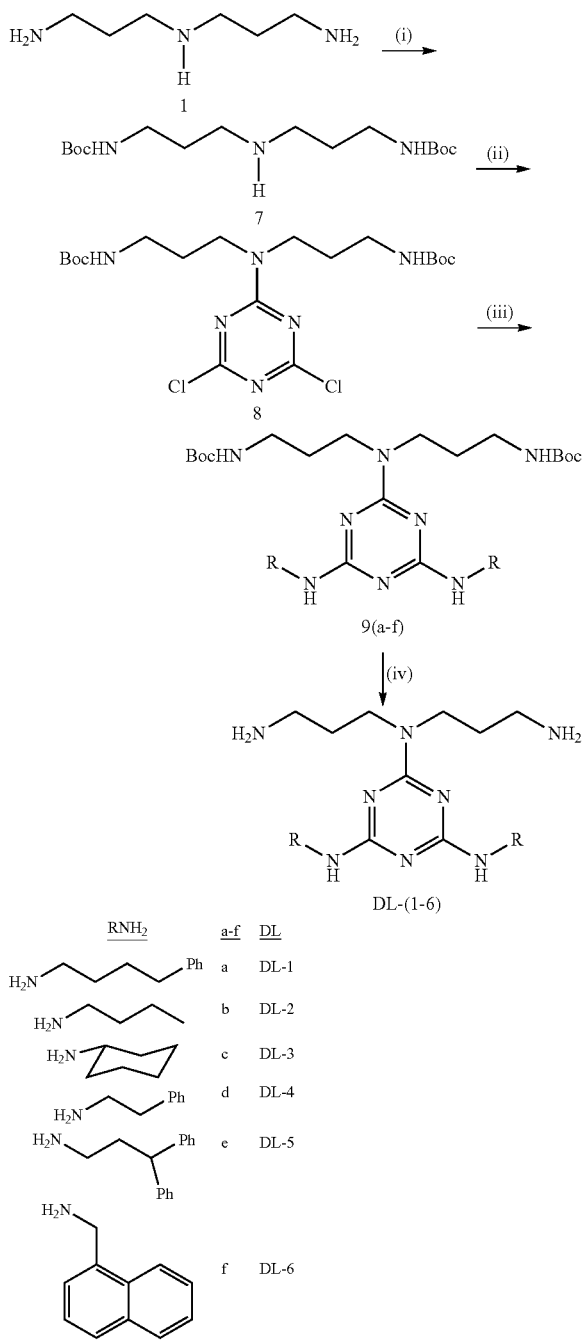

Step 1.

The solution (in THF, 75 mL), in which 1-(tert-butoxy-carbonyloxyimino)-2-phenylacetonitrile (BOC-ON, 25 g, 0.100 mol, 2.0 equiv.) was dissolved, was slowly inputted into 3,3'-diaminodipropylamine (7.05 mL, 0.051 mol, 1.0 equiv.) and diisopropylethylamine (DIEA, 25 mL, 0.142 mol, 2.8 equiv.) dissolved in tetrahydrofuran (THF, 125 mL), at 0° C., and reacted at the same temperature for three hours. After that, the temperature was raised up to room temperature (23° C.) and reacted for 20 hours.

The reaction solution was concentrated, after which the residue was redissolved in dichloromethane (100 mL), washed, dried and concentrated. The product was treated with hexane (125 mL) and methanol (1 mL) and stored at a low temperature, after which the resulting solid was filtered, washed and dried to obtain the compound 7 (13 g, 81%).

$^1$H NMR (400 MHz, CDCl$_3$) δ 5.19 (s, 2H), 3.21 (q, J=6.3 Hz, 4H), 2.65 (t, J=6.5 Hz, 4H), 1.65 (p, J=6.5 Hz, 4H), 1.44 (s, 18H). $^{13}$C NMR (100 MHz, CDCl$_3$) δ 156.1, 78.9, 47.4, 38.9, 29.8. Maldi-tof m/z calcd for C$_{16}$H$_{33}$N$_3$O$_4$: 331.2, found 332.2 (M+H)$^+$

Step 2.

Cyanuric chloride 4 (1 g, 5.43 mmol, 1 equiv.) and diisopropylethylamine (2.8 mL, 16.3 mmol, 3 equiv.) dissolved in dichloromethane (30 mL) was slowly inputted into the solution (in DCM, 20 mL) in which the compound 7 (1.83 g, 5.54 mmol, 1.02 equiv.) was dissolved for 30 minutes, at 0° C. The reaction solution was reacted at the same temperature for three hours.

Water (50 mL) was inputted into the reaction solution to terminate the reaction, and then an extraction was performed twice with dichloromethane. The extracted solution was dried, concentrated, and purified using column chromatography (Hexane:Ethyl acetate=3:1) to obtain the compound 8 (2.26 g, 87%).

$^1$H NMR (400 MHz, CDCl$_3$) δ 5.05 (t, J=6.0 Hz, 2H), 3.63 (t, J=6.9 Hz, 4H), 3.13 (q, J=6.4 Hz, 4H), 1.81 (p, J=6.7 Hz, 4H), 1.45 (s, 18H). $^{13}$C NMR (100 MHz, CDCl$_3$) δ 170.1, 164.7, 156.0, 79.3, 45.0, 37.4, 28.4, 27.7.

Step 3.

Phenylbutylamine (a) (0.151 mL, 1.014 mmol, 3.00 equiv.) dissolved in dioxane (1,4-dioxane, 10 mL) was slowly inputted into the solution (in 1,4-dioxane, 20 mL) in which the compound 8 (162 mg, 0.338 mmol, 1 equiv.) and diisopropylethylamine (0.175 ml, 1.014 mmol, 3 equiv.) were dissolved, at 0° C. After that, the temperature was raised to room temperature (23° C.), reacted for one hour, and reacted for 13 hours under reflux condition.

The reaction solution was concentrated, after which an extraction was performed with dichloromethane (30 mL). The extracted solution was dried, concentrated, and purified using column chromatography (hexane:ethylacetate=7:3) to obtain the compound 9a (176 mg, 74%).

$^1$H NMR (400 MHz, CDCl$_3$) δ 7.29 (d, J=6.6 Hz, 5H), 7.19 (t, J=6.6 Hz, 5H), 5.33-4.76 (m, 2H), 3.66-3.47 (m, 4H), 3.48-3.33 (m, 4H), 3.08 (q, J=6.3 Hz, 4H), 2.66 (t, J=7.5 Hz, 4H), 2.17-1.99 (m, 2H), 1.72 (t, J=7.5 Hz, 8H), 1.67-1.57 (m, 4H), 1.46 (s, 18H). 13C NMR (100 MHz, CDCl$_3$) δ 195.6, 165.2, 156.0, 142.2, 128.4, 128.4, 128.3, 125.8, 78.9, 43.5, 42.2, 40.6, 36.9, 35.6, 31.5, 28.5, 27.5, 25.6.

Step 4.

The compound 9a was dissolved in an organic solvent (TFA:DCM (7.5:2.5 mL)) and reacted at room temperature for four hours.

The reaction solution was concentrated, after which cold diethyl ether was inputted thereinto, and the formed precipitate was separated by centrifugation. The precipitate was redissolved in acetonitrile, after which the solvent was removed therefrom to obtain DL-1 (110 mg, 73%).

¹H NMR (500 MHz, MeOD) δ 7.27 (t, J=7.4 Hz, 4H), 7.21 (d, J=7.6 Hz, 4H), 7.17 (t, J=7.4 Hz, 2H), 4.16 (s, 1H), 3.86-3.64 (m, 5H), 3.55-3.35 (m, 4H), 3.16-2.92 (m, 5H), 2.69 (t, J=7.2 Hz, 4H), 2.05 (d, J=9.2 Hz, 4H), 1.80-1.57 (m, 8H). ¹³C NMR (100 MHz, MeOD) δ 161.0, 154.4, 142.0, 128.2, 128.0, 125.5, 56.3, 44.9, 40.6, 37.4, 35.1, 28.5, 25.8. Maldi-tof m/z calcd for $C_{29}H_{44}N_8$: 504.3, found 505.2 $(M+H)^+$ Examples 8 to 12

DL-2 to DL-6 were prepared by a method similar to the method of above Example 8.

The structural analysis data of the obtained 9b to 9f and DL-2 to DL-6 are shown in the table 2 below.

TABLE 2

| | Compound | Yield (%), ¹H-NMR |
|---|---|---|
| Example 8 | 9b | (175 mg, 93%). ¹H NMR (500 MHz, CDCl₃) δ 4.81 (s, 2H), 3.57 (s, 4H), 3.41 (s, 4H), 3.09 (s, 4H), 1.73 (s, 4H), 1.58 (dt, J = 14.1, 6.6 Hz, 4H), 1.48 (s, 18H), 1.54-1.43 (m, 5H), 0.96 (t, J= 7.3 Hz, 6H). ¹³C NMR (100 MHz, CDCl₃) δ 174.0, 165.7, 156.0, 78.8, 42.2, 40.4, 36.8, 32.0, 28.5, 28.4, 27.5, 20.1, 13.9. |
| | DL-2 | (31 mg, 86%). ¹H NMR (500 MHz, MeOD) δ 3.78 (t, J = 7.2 Hz, 4H), 3.46 (t, J = 6.9 Hz, 3H), 3.37 (d, J = 5.3 Hz, 1H), 3.02 (t, J = 7.8 Hz, 4H), 2.16-1.99 (m, 4H), 1.64 (p, J = 7.1 Hz, 4H), 1.45 (h, J = 6.9 Hz, 4H), 1.00 (t, J = 7.3 Hz, 6H). ¹³C NMR (100 MHz, MeOD) δ 162.8, 154.5, 44.8, 40.4, 37.4, 30.7, 25.8, 19.7, 12.8. Maldi-tof m/z calcd for $C_{17}H_{36}N_8$: 352.3, found 353.1 $(M + H)^-$ |
| Example 9 | 9c | (193 mg, 69%). ¹H NMR (500 MHz, CDCl₃) δ 4.71 (s, 2H), 3.84-3.77 (m, 2H), 3.64-3.40 (m, 4H), 3.23-2.93 (m, 4H), 2.06-1.91 (m, 4H), 1.87-1.61 (m, 10H), 1.54-1.43 (m, 18H), 1.39 (q, J = 12.8, 12.4 Hz, 5H), 1.25-1.05 (m, 5H). ¹³C NMR (100 MHz, CDCl₃) δ 165.1, 156.0, 79.0, 72.8, 49.3, 49.1, 36.4, 34.0, 33.5, 28.6, 27.4, 25.7, 24.7. |
| | DL-3 | (32 mg, 83%). ¹H NMR (500 MHz, MeOD) δ 4.00-3.59 (m, 6H), 3.02 (t, J = 7.7 Hz, 4H), 2.15-2.03 (m, 4H), 2.00 (dd, J = 10.9, 5.9 Hz, 4H), 1.89-1.77 (m, 4H), 1.74-1.59 (m, 2H), 1.54-1.22 (m, 10H). ¹³C NMR (100 MHz, MeOD) δ 162.7, 153.6, 50.1, 44.9, 37.5, 31.9, 25.9, 25.2, 24.3. Maldi-tof m/z calcd for $C_{21}H_{40}N_8$: 404.3, found 405.2 $(M + H)^-$ |
| Example 10 | 9d | (242 mg, 85%). ¹H NMR (500 MHz, CDCl₃) δ 7.32 (t, J = 7.5 Hz, 4H), 7.24 (t, J = 7.2 Hz, 6H), 6.88 (s, 1H), 5.21 (s, 1H), 4.91 (s, 1H), 3.77-3.45 (m, 8H), 3.23-3.02 (m, 4H), 3.01-2.80 (m, 4H), 1.99 (s, 1H), 1.85-1.64 (m, 4H), 1.44 (s, 18H). ¹³C NMR (100 MHz, CDCl₃) δ 165.8, 156.0, 139.3, 128.8, 128.6, 126.4, 79.4, 51.8, 42.5, 29.9, 28.5, 27.4, 25.6 |
| | DL-4 | (51 mg, 84%). ¹H NMR (500 MHz, MeOD) δ 7.37-7.26 (m, 8H), 7.24 (t, J = 7.3 Hz, 2H), 3.73 (dt, J = 20.1, 7.0 Hz, 8H), 3.00 (t, J = 8.0 Hz, 4H), 2.95 (t, J = 7.0 Hz, 4H), 2.13-2.00 (m, 4H). ¹³C NMR (100 MHz, MeOD) δ 162.2, 157.3, 154.5, 138.6, 128.6, 128.3, 126.3, 45.5, 41.9, 39.0, 34.9, 26.8. Maldi-tof m/z calcd for $C_{25}H_{36}N_8$: 448.3, found 449.2 $(M + H)^-$ |
| Example 11 | 9e | (765 mg, 85%). ¹H NMR (400 MHz, CDCl₃) δ 7.26-7.04 (m, 20H), 6.77 (s, 1H), 4.91 (s, 2H), 4.00-3.83 (m, 2H), 3.48-3.30 (m, 4H), 3.30-3.12 (m, 4H), 3.04-2.84 (m, 4H), 2.25 (q, J = 7.3 Hz, 4H), 1.68-1.51 (m, 4H), 1.45-1.26 (m, 18H). ¹³C NMR (100 MHz, CDCl₃) δ 165.9, 156.0, 144.5, 128.5, 127.9, 126.3, 78.8, 48.6, 42.6, 39.3, 37.0, 35.7, 28.5, 27.7. |
| | DL-5 | (58 mg, 72%). ¹H NMR (400 MHz, MeOD) δ 7.26-7.12 (m, 16H), 7.07 (d, J = 7.5 Hz, 4H), 3.96 (t, J = 7.7 Hz, 2H), 3.63-3.23 (m, 7H), 3.00-2.60 (m, 4H), 2.36-2.18 (m, 4H), 1.99-1.73 (m, 4H). ¹³C NMR (100 MHz, MeOD) δ 162.5, 154.4, 144.4, 128.3, 128.3, 127.5, 126.1, 48.5, 44.5, 39.2, 37.2, 34.4, 25.7. Maldi-tof m/z calcd for $C_{39}H_{48}N_8$: 628.4, found 629.4 $(M + H)^-$ |
| Example 12 | 9f | (640 mg, 86%). ¹H NMR (500 MHz, CDCl₃) δ 8.16-8.04 (m, 2H), 7.94-7.85 (m, 2H), 7.81 (d, J = 8.0 Hz, 2H), 7.61-7.37 (m, 8H), 6.77 (s, 1H), 5.47-5.15 (m, 2H), 5.11 (s, 4H), 3.67-3.43 (m, 4H), 3.19-2.90 (m, 4H), 1.86-1.73 (m, 4H), 1.40 1.15 (m, 18H). ¹³C NMR (100 MHz, CDCl₃) δ 193.6, 165.9, 165.5, 156.0, 134.4, 133.8, 131.5, 128.7, 128.1, 126.4, 125.8, 125.4, 123.5, 78.7, 42.7, 36.7, 29.7, 27.5. |
| | DL-6 | (39 mg, 81%). ¹H NMR (400 MHz, MeOD) δ 8.13 (d, J = 8.4 Hz, 2H), 7.96 (d, J = 8.0 Hz, 2H), 7.89 (d, J = 8.0 Hz, 2H), 7.67-7.41 (m, 8H), 5.13 (s, 4H), 3.67 (t, J= 7.2 Hz, 4H), 3.10-2.95 (m, 1H), 2.72 (t, J = 7.5 Hz, 3H), 1.96 (tt, J = 15.1, 9.1 Hz, 4H). ¹³C NMR (100 MHz, MeOD) δ 162.6, 154.6, 134.0, 132.4, 131.1, 128.6, 128.2, 126.4, 125.8, 125.5, 125.2, 122.7, 44.8, 42.4, 37.0, 25.5. Maldi-tof m/z calcd for $C_{31}H_{36}N_8$: 520.3, found 521.0 $(M + H)^-$ (rotamer existence were present in both proton and carbon) |

Example 13

Second Phase Derivatisation_DG Series

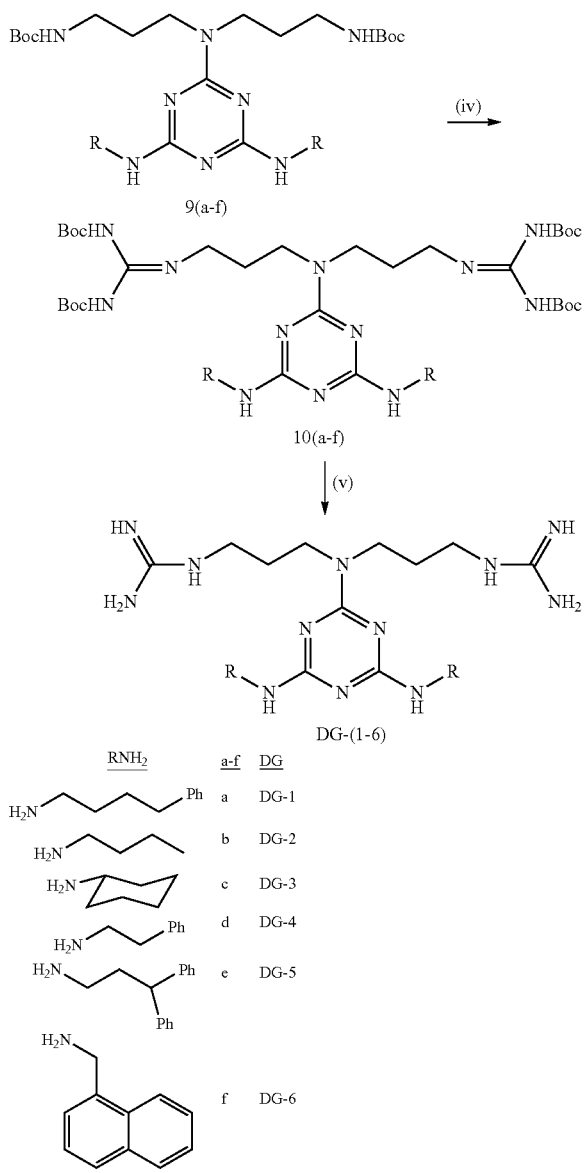

Step 1.

The compound 9a (156 mg, 0.221 mmol) was dissolved in an organic solvent (TFA:DCM (7.5:2.5 mL)) and reacted at room temperature for four hours. The reaction solution was concentrated and redissolved in dichloromethane (20 mL). The reaction solution was cooled down to 0° C., and a solution, in which triethylamine (0.32 mL, 2.21 mmol, 10 equiv.) was dissolved (in DCM, 5 mL), was slowly inputted. After that, N,N'-di-boc-N-trifylguanidine 2 (216 mg, 0.552 mmol, 2.5 equiv.) dissolved in dichloromethane (5 mL) was added thereto at 0° C. After that, the temperature was raised up to room temperature and reacted for six hours.

Water (20 mL) was inputted into the reaction solution to terminate the reaction, and an extraction was performed three times with dichloromethane. The extracted solution was dried, concentrated, and purified using column chromatography (hexane:ethylacetate=3:1) to obtain the compound 10a (209 mg, 96%).

$^1$H NMR (400 MHz, CDCl$_3$) δ 1H NMR (400 MHz, CDCl$_3$) δ 11.73 (s, 2H), 8.86 (s, 2H), 7.24 (t, J=7.3 Hz, 4H), 7.20-7.08 (m, 6H), 6.06 (s, 2H), 3.50 (t, J=5.9 Hz, 4H), 3.46-3.26 (m, 8H), 2.61 (t, J=7.3 Hz, 4H), 1.78-1.56 (m, 12H), 1.52-1.45 (m, 36H). $^{13}$C NMR (100 MHz, CDCl$_3$) δ 166.3, 163.9, 156.7, 155.7, 153.1, 142.4, 128.4, 128.3, 125.7, 83.0, 79.2, 40.5, 35.7, 30.0, 28.9, 28.4, 28.3, 28.1, 27.9. (Rotomer existence is present)

Step 2.

The compound 10a (110 mg, 0.111 mmol) was dissolved in an organic solvent (TFA:DCM (7.5:2.5 mL)) and reacted at room temperature for four hours.

The reaction solution was concentrated, after which cold diethyl ether was inputted thereinto, and the formed precipitate was separated by centrifugation. The precipitate was redissolved in acetonitrile, after which the solvent was removed therefrom to obtain DG-1 (40 mg, 65%).

$^1$H NMR (500 MHz, MeOD) δ 7.26 (t, J=7.5 Hz, 4H), 7.22-7.13 (m, 6H), 3.70 (t, J=7.4 Hz, 4H), 3.45 (d, J=6.7 Hz, 4H), 3.25 (t, J=6.9 Hz, 4H), 2.68 (t, J=7.2 Hz, 4H), 1.96 (p, J=7.1 Hz, 4H), 1.79-1.57 (m, 8H). $^{13}$C NMR (100 MHz, MeOD) δ 162.4, 157.3, 154.4, 142.0, 128.1, 128.0, 125.5, 45.3, 40.4, 38.9, 35.1, 28.4, 28.1, 26.8. Maldi-tof m/z calcd for C$_{31}$H$_{48}$N$_{12}$: 588.4, found 589.1 (M+H)$^+$

Examples 14 to 18

DG-2 to DG-6 were prepared by a method similar to the method of above Example 13.

The structural analysis data of the obtained 10b to 10f and DG-2 to DG-6 are shown in the table 3 below.

TABLE 3

| Compound | | Yield (%), $^1$H-NMR |
|---|---|---|
| Example 14 | 10b | (162 mg, 94%). $^1$H NMR (400 MHz, CDCl$_3$) δ 8.85 (s, 2H), 8.39 (s, 1H), 6.02 (s, 1H), 3.63-3.25 (m, 12H), 1.93-1.65 (m, 4H), 1.54 (s, 9H), 1.53 (s, 9H), 1.50-1.48 (m, 27H), 1.35 (h, J = 7.4 Hz, 4H), 0.91 (t, J = 7.3 Hz, 6H). $^{13}$C NMR (100 MHz, CDCl$_3$) δ 163.8, 153.1, 151.6, 149.1, 85.8, 83.1, 79.3, 40.4, 31.2, 28.3, 28.1, 28.0, 27.8, 20.1, 13.9. |
| | DG-2 | (50 mg, 68%).$^1$H NMR (500 MHz, MeOD) δ 7.61 (s, 1H), 3.76 (t, J = 7.3 Hz, 4H), 3.45 (t, J = 6.8 Hz, 4H), 3.29 (d, J = 6.5 Hz, 4H), 2.15-1.84 (m, 4H), 1.62 (q, J = 7.2 Hz, 4H), 1.44 (q, J = 7.5 Hz, 4H), 0.99 (t, J = 7.3 Hz, 6H). $^{13}$C NMR (100 MHz, MeOD) δ 162.5, 157.3, 154.5, 45.4, 40.3, 38.9, 30.8, 26.8, 19.7, 12.8. Maldi-tof m/z calcd for C$_{19}$H$_{40}$N$_{12}$: 436.3 found 437.7 (M + H)$^-$ |

TABLE 3-continued

| Compound | | Yield (%), ¹H-NMR |
|---|---|---|
| Example 15 | 10c | (147 mg, 87%). ¹H NMR (400 MHz, CDCl$_3$) δ 8.78 (s, 2H), 5.57 (s, 2H), 3.88-3.73 (m, 2H), 3.59-3.33 (m, 8H), 2.11-1.91 (m, 4H), 1.77-1.65 (m, 6H), 1.59-1.46 (m, 42H), 1.41-1.30 (m, 4H), 1.23-1.09 (m, 4H). ¹³C NMR (101 MHz, CDCl$_3$) δ 165.4, 163.9, 153.0, 151.9, 85.9, 82.9, 79.2, 37.4, 33.6, 31.6, 28.3, 27.8, 25.4, 22.7, 14.1. |
| | DG-3 | (34 mg, 57%). ¹H NMR (500 MHz, MeOD) δ 3.98-3.82 (m, 2H), 3.79-3.63 (m, 4H), 3.28 (d, J = 6.3 Hz, 4H), 1.99 (t, J = 11.0 Hz, 8H), 1.87-1.76 (m, 4H), 1.72-1.62 (m, 2H), 1.50-1.25 (m, 10H). ¹³C NMR (100 MHz, MeOD) δ 162.4, 157.3, 153.5, 50.0, 45.6, 39.0, 31.9, 26.9, 25.1, 24.3. Maldi-tof m/z calcd for C$_{23}$H$_{44}$N$_{12}$: 488.3, found 490.8 (M + H)$^-$ |
| Example 16 | 10d | (172 mg, 82%). ¹H NMR (500 MHz, CDCl$_3$) δ 8.87 (s, 2H), 7.29-7.21 (m, 4H), 7.19 (d, J = 6.9 Hz, 2H), 7.14 (d, J = 7.4 Hz, 4H), 6.35-5.98 (m, 2H), 3.69-3.48 (m, 8H), 3.48-3.28 (m, 4H), 2.91 (t, J = 7.5 Hz, 4H), 1.78-1.61 (m, 4H), 1.51 (d, J = 4.2 Hz, 18H), 1.47 (s, 18H). ¹³C NMR (100 MHz, CDCl$_3$) δ 166.2, 163.9, 155.7, 153.1, 148.7, 139.8, 128.8, 128.4, 126.2, 82.9, 79.2, 42.7, 41.1, 36.7, 28.4, 28.1, 28.0, 27.8. |
| | DG-4 | (45 mg, 56%). ¹H NMR (500 MHz, MeOD) δ 7.62 (s, 1H), 7.31 (t, J = 7.4 Hz, 4H), 7.29-7.18 (m, 6H), 3.71 (q, J = 7.3 Hz, 8H), 3.31-3.19 (m, 4H), 2.94 (t, J = 6.9 Hz, 4H), 1.98 (t, J = 7.3 Hz, 4H). ¹³C NMR (100 MHz, MeOD) δ 162.2, 157.3, 154.5, 138.6, 128.6, 128.3, 126.3, 45.5, 41.9, 39.0, 34.9, 26.8. Maldi-tof m/z calcd for C$_{27}$H$_{40}$N$_{12}$: 532.3, found 533.8 (M + H)$^-$ |
| Example 17 | 10e | (181 mg, 88%). ¹H NMR (400 MHz, CDCl$_3$) δ 11.72 (s, 2H), 8.84 (s, 2H), 7.28-7.19 (m, 11H), 7.15 (d, J = 7.4 Hz, 9H), 6.04 (s, 2H), 3.90 (s, 2H), 3.61-3.33 (m, 8H), 3.32-3.13 (m, 4H), 2.31 (q, J = 7.6 Hz, 4H), 1.66 (d, J = 19.7 Hz, 6H), 1.50 (s, 18H), 1.39 (s, 16H) ¹³C NMR (100 MHz, CDCl$_3$) δ 171.2, 166.3, 163.9, 155.7, 153.1, 144.7, 128.4, 127.8, 126.1, 83.0, 79.2, 60.4, 48.8, 41.3, 39.6, 37.2, 35.8, 28.4, 27.7, 21.1, 14.2. |
| | DG-5 | (55.2 mg, 72%). ¹H NMR (500 MHz, MeOD) δ 7.30 (d, J = 6.8 Hz, 16H), 7.18 (t, J = 6.9 Hz, 5H), 4.12-4.02 (m, 2H), 3.69-3.53 (m, 5H), 3.44 (t, J = 7.0 Hz, 4H), 3.12 (t, J = 7.1 Hz, 4H), 2.42 (q, J = 7.2 Hz, 5H), 2.02-1.89 (m, 2H), 1.86 (t, J = 7.2 Hz, 4H). ¹³C NMR (100 MHz, MeOD) δ 162.2, 157.2, 154.4, 144.4, 128.2, 127.5, 126.0, 48.5, 45.2, 39.1, 38.9, 34.3, 26.7. Maldi-tof m/z calcd for C$_{41}$H$_{52}$N$_{12}$: 712.4, found 713.4 (M + H)$^-$ (exist as rotomer) |
| Example 18 | 10f | (163 mg, 89%). ¹H NMR (500 MHz, CDCl$_3$) δ 11.72-11.39 (m, 2H), 9.00-8.79 (m, 2H), 8.06 (d, J = 8.3 Hz, 2H), 7.85 (d, J = 8.3 Hz, 2H), 7.74 (d, J = 8.3 Hz, 2H), 7.56-7.31 (m, 8H), 6.42 (d, J = 6.3 Hz, 2H), 5.08 (s, J = 17.6, 9.3 Hz, 4H), 3.58 (t, J = 6.1 Hz, 4H), 3.52-3.29 (m, 4H), 1.90-1.66 (m, 4H), 1.53 (s, 18H), 1.31-1.26 (m, 4H), 1.21 (s, 14H). (4 Boc groups exist as rotomer) ¹³C NMR (100 MHz, CDCl$_3$) δ 166.4, 163.9, 155.7, 153.0, 135.1, 133.7, 131.5, 128.5, 127.7, 126.1, 125.6, 125.5, 125.4, 123.5, 83.0, 79.1, 42.6, 41.4, 37.2, 28.4, 27.8 (traces of dichloromethane is present). |
| | DG-6 | (52 mg, 78%). ¹H NMR (500 MHz, MeOD) δ 8.11 (d, J = 8.4 Hz, 2H), 7.95 (d, J = 8.1 Hz, 2H), 7.88 (d, J = 8.2 Hz, 2H), 7.61 (t, J = 7.5 Hz, 2H), 7.58-7.52 (m, 4H), 7.49 (t, J = 7.5 Hz, 2H), 5.16-5.09 (m, 4H), 3.67 (t, J = 7.4 Hz, 4H), 3.30-3.18 (m, 1H), 2.98 (t, J = 7.1 Hz, 3H), 1.95 (s, 1H), 1.81 (t, J = 7.8 Hz, 4H). ¹³C NMR (100 MHz, MeOD) δ 162.3, 157.1, 154.5, 134.0, 132.5, 131.1, 128.6, 128.2, 126.3, 125.7, 125.5, 125.1, 122.7, 45.4, 42.3, 38.7, 26.6. Maldi-tof m/z calcd for C$_{41}$H$_{52}$N$_{12}$: 604.3, found 605.3 (M + H)$^-$ |

TABLE 4

| Example | MIC$^a$ (μM) | | | | GM (μM)$^b$ | MHC (μM)$^c$ | TI (MHC/GM)$^d$ |
|---|---|---|---|---|---|---|---|
| | Gram-negative bacteria | | Gram-positive bacteria | | | | |
| | *Escherichia coli* (KCTC1682) | *Pseudomonas aeruginosa* (KCTC 1637) | *Staphylococcus epidermidis* (KCTC 1917) | *Staphylococcus aureus* (KCTC 1621) | | | |
| First phase derivatisation | | | | | | | |
| Example 1 (MG-1) | >160 | 80 | >160 | 40 | 190 | >320 | 16.0 |
| Example 2 (MG-2) | >160 | 80 | >160 | 20 | 185 | >320 | 3.5 |
| Example 3 (MG-3) | 160 | 40 | 160 | 10 | 92.5 | >320 | 6.9 |
| Example 4 (MG-4) | 160 | 20 | 80 | 5 | 66.3 | >320 | 9.7 |
| Example 5 (MG-5) | 160 | 160 | 160 | 5 | 121.5 | >320 | 5.3 |
| Example 6 (MG-6) | 40 | 10 | 40 | 5 | 95.0 | >320 | 6.7 |
| Second phase derivatisation | | | | | | | |
| Example 7 (DL-1) | 20 | 10 | 10 | 2.5 | 10.6 | 88 | 8.3 |
| Example 8 (DL-2) | >160 | 10 | >160 | 80 | 182.5 | >320 | 3.5 |
| Example 9 (DL-3) | 160 | 10 | 160 | 10 | 85.0 | >320 | 7.5 |
| Example 10 (DL-4) | 160 | 20 | 160 | 10 | 87.5 | >320 | 7.3 |
| Example 11 (DL-5) | 5 | 5 | 5 | 2.5 | 4.4 | 185 | 42.0 |
| Example 12 (DL-6) | 5 | 10 | 20 | 2.5 | 9.4 | >320 | 68.1 |
| Example 13 (DG-1) | 5 | 10 | 10 | 2.5 | 6.9 | 177 | 25.7 |
| Example 14 (DG-2) | 160 | 20 | 160 | 10 | 87.5 | >320 | 7.3 |
| Example 15 (DG-3) | 10 | 10 | 10 | 2.5 | 8.1 | >320 | 79.0 |
| Example 16 (DG-4) | 40 | 10 | 20 | 2.5 | 18.1 | >320 | 35.4 |
| Example 17 (DG-5) | 5 | 5 | 10 | 2.5 | 5.6 | 140 | 25.0 |
| Example 18 (DG-6) | 5 | 10 | 10 | 2.5 | 6.9 | 88 | 12.8 |
| Control (Melittin) | 2.5 | 5 | 5 | 2.5 | 3.8 | 4 | 1.1 |

As shown in FIG. 1, all of the triazine compounds according to the present invention were not confirmed to be cytotoxic.

In addition, as a result of confirming the hemolytic action of the triazine compound according to the present invention, all did not show hemolysis up to a concentration of 80 μM/well in which 100% hemolysis was induced by melittine, and less than 8% of hemolysis was induced at the test concentration. The above results suggest that the triazine compound according to the present invention has very high stability to the skin and exhibits an excellent antibacterial effect.

As shown in the table 4, it was confirmed that the triazine compound according to the present invention shows excellent antibacterial activity in both gram-negative bacteria and gram-positive bacteria. In particular, it was confirmed that the anti-inflammatory effect is also enhanced as the hydrophobicity of the triazine compound according to the present invention increases. The above results suggest that the antibacterial activity can be optimized by increasing the hydrophobicity or decreasing the electric charges of the triazine compound according to the present invention.

Figure 2:
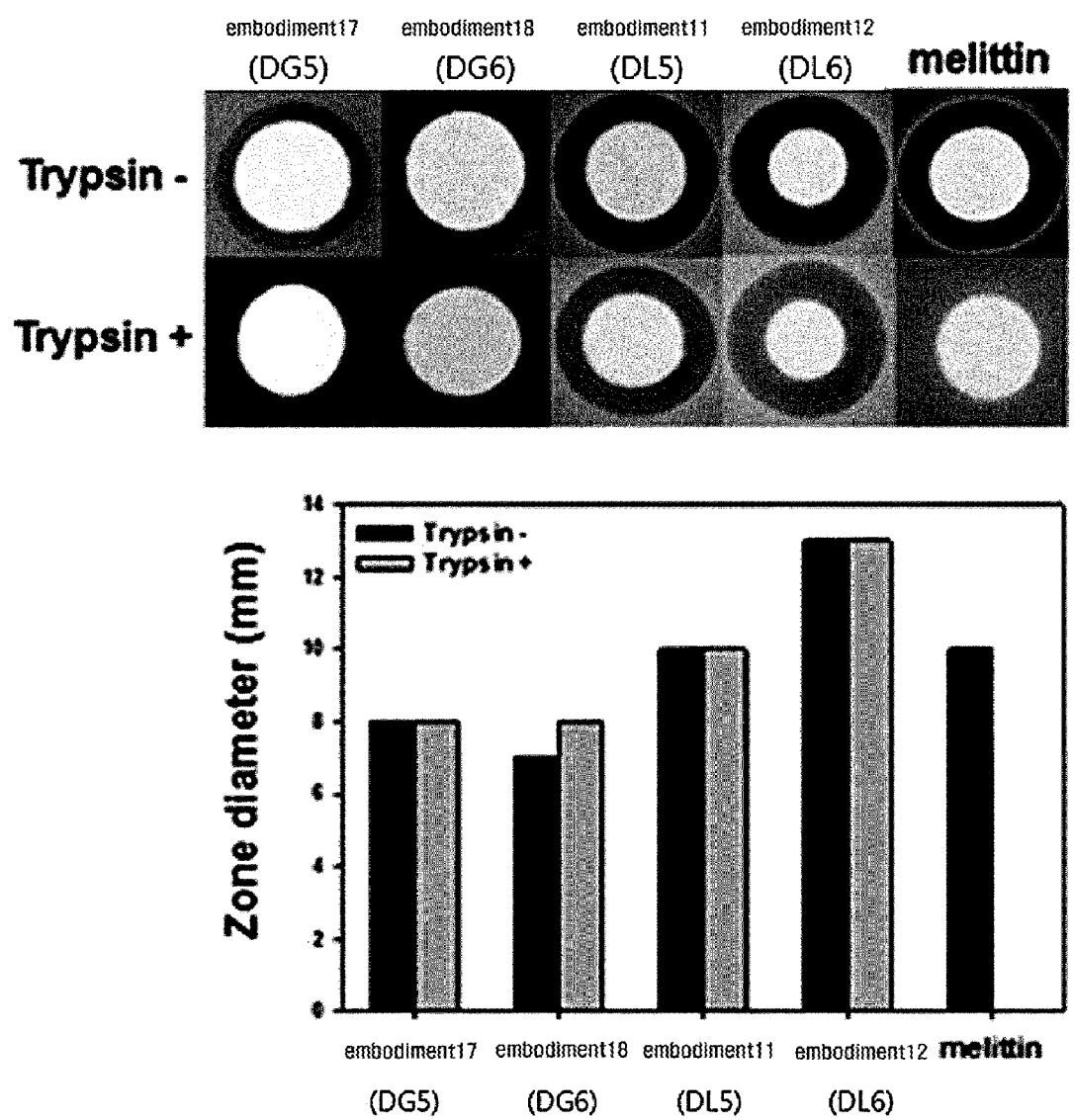
FIG. 2 is a view showing the results of identifying the stability of the triazine compound according to the present invention against protease.

As shown in FIG. 2, it was confirmed that Examples 11, 12, 17 and 18 do not lose the antibacterial activity against *E. coli* for 24 hours after trypsin culture, but melittin, a control group, shows a remarkable decrease in the antibacterial activity due to protein degradation by trypsin.

In other words, the triazine compound according to the present invention can maintain the antibacterial activity even after protease treatment and thus stably implement the antibacterial activity.

Figure 3:
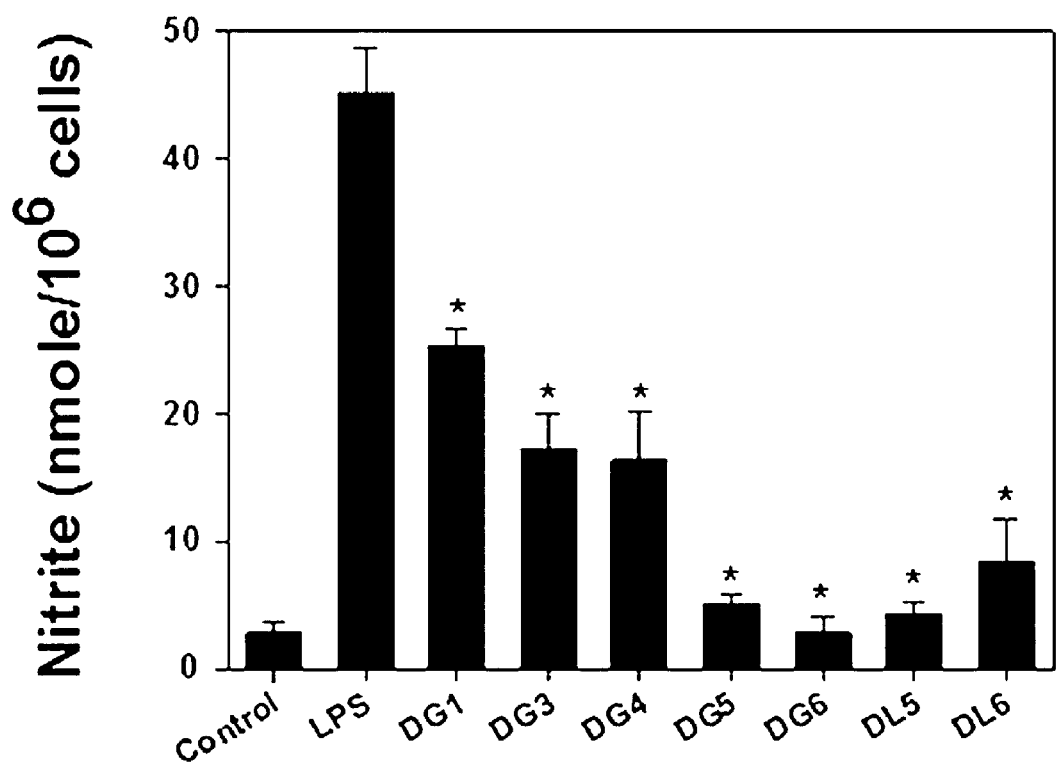
FIG. 3 is a view showing the results of identifying an inhibitory effect of the triazine compound according to the present invention on NO production.

As shown in FIG. 3, it was confirmed that the triazine compound according to the present invention effectively inhibits the production of NO, which is mainly caused in inflammations. In particular, it was confirmed that Examples 11 and 12 and Examples 17 and 18 can more effectively inhibit the production of NO.

Figure 4:
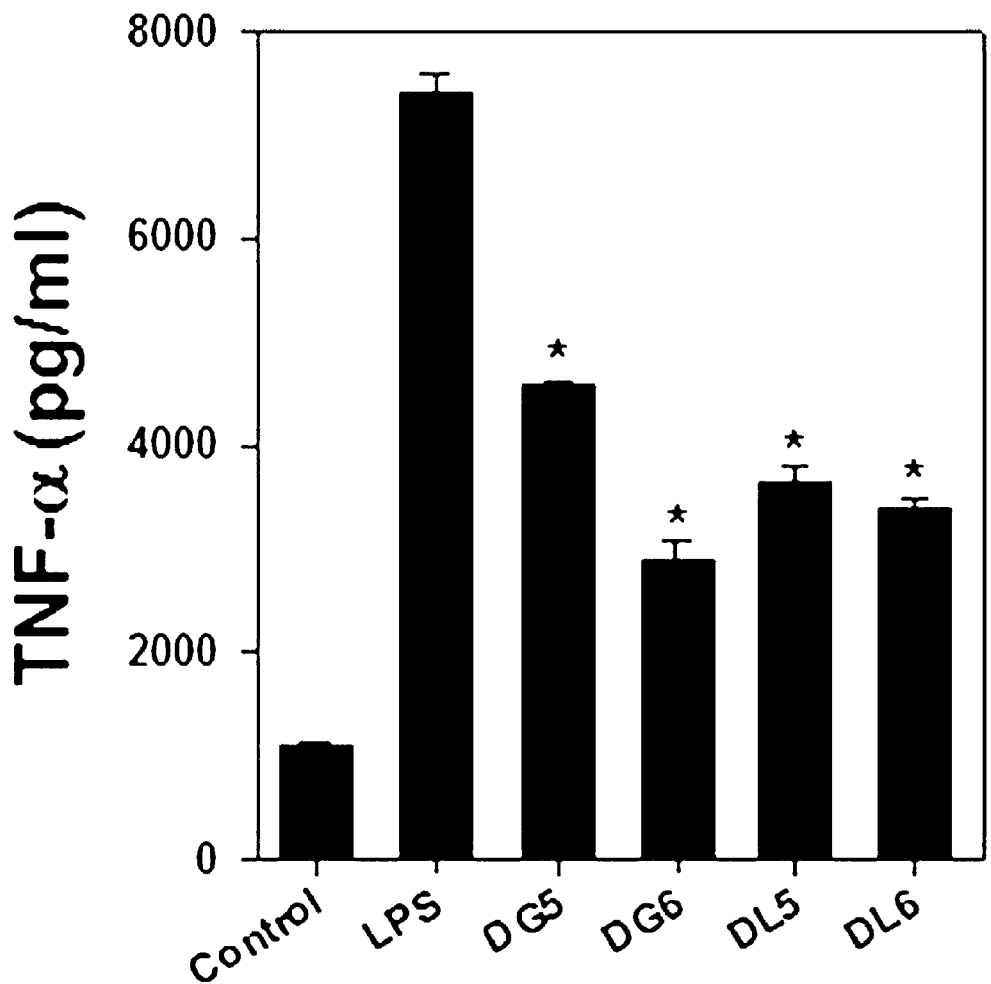
FIG. 4 is a view showing the results of identifying an inhibitory effect of the triazine compound according to the present invention on TNF-α production.

In addition, it was confirmed that the triazine compound according to the present invention can significantly inhibit the production of TNF-α, one of the inflammatory cytokines, compared to the control group (see FIG. 4).

In addition, as a result of confirming the effect of alleviating atopic dermatitis, it was confirmed that the triazine compound according to the present invention significantly reduces the thickness of the treated lesion site.

Figure 5:
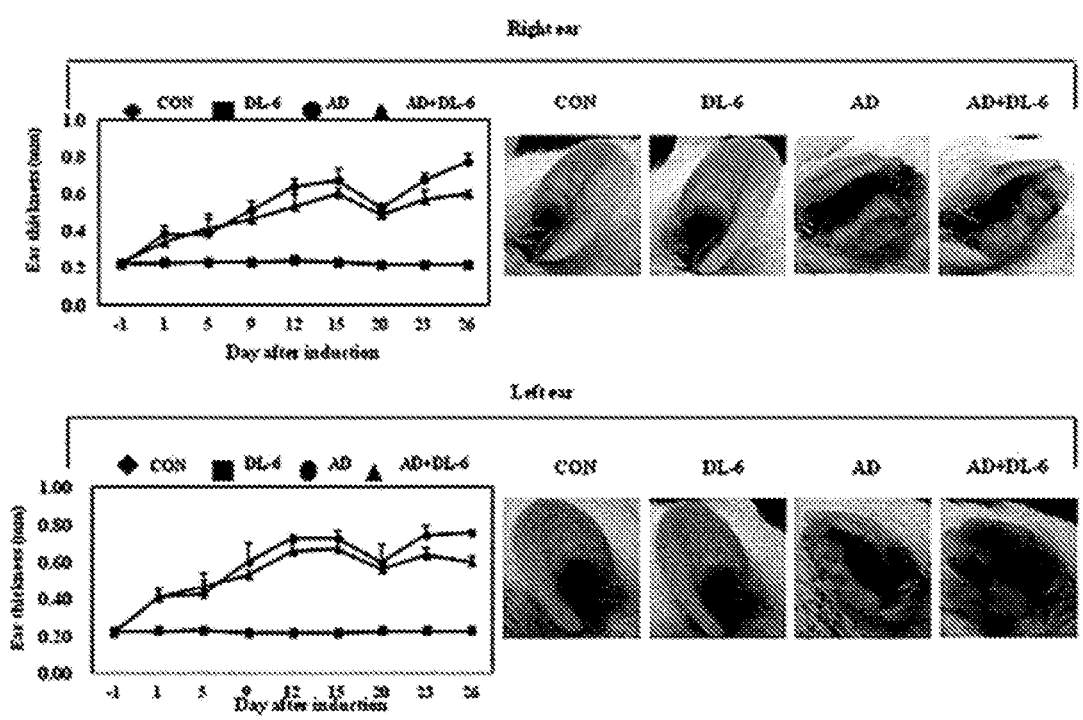
FIG. 5 is a view and an image showing the results of observing a thickness of a lesion site with induced atopic dermatitis, which is treated with the triazine compound according to the present invention.
Figure 6:
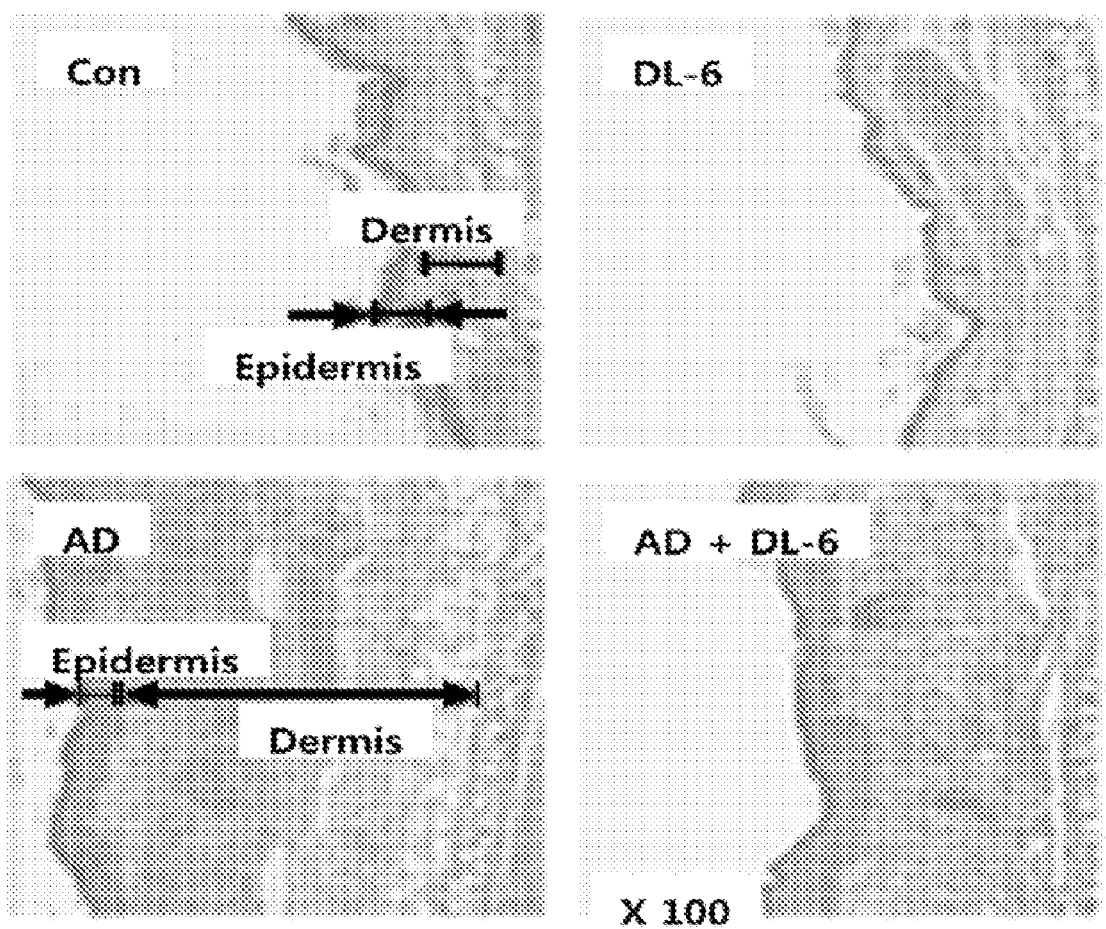
FIG. 6 is an image showing the results of observing skin on a lesion site with induced atopic dermatitis, which is treated with the triazine compound according to the present invention, after dying the skin through Hematoxylin & Eosin (H&E) staining protocol.

In particular, as a result of observing the skin dyed by the Hematoxylin and Eosin (H&E) staining method with an optical microscope, it was confirmed that the thickness of stratum corneum and epidermal layer at each lesion site is significantly reduced (see FIGS. 5 and 6). Specifically, in the case of Example 16 (AD+DL-6), it was confirmed that the thickness of epidermis is decreased by 30% or more and the thickness of dermis is decreased by 50% or more compared to the lesion (AD) with induced atopic dermatitis.

As described above, the present invention has been described by specific matters and limited embodiments, but they are provided only to help a more general understanding of the present invention, and the present invention is not limited to the above embodiments, and those skilled in the art to which the present invention pertains can make various modifications and variations from these descriptions.

Accordingly, the scope of the present invention is not to be limited to the described embodiments, and all those having equal or equivalent modifications to the claims as well as the claims to be described later fall within the scope of the present invention.

The invention claimed is:

1. A triazine compound represented by a following formula 2:

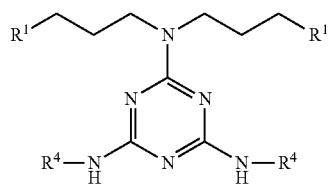

[Formula 2]

wherein $R^1$ and $R^2$ are each independently *—$N(R^{11})(R^{12})$ or guanidine, and the $R^{11}$ and $R^{12}$ are each independently hydrogen or $C_1$-$C_{30}$ alkyl; and $R^4$ is each independently $C_1$-$C_{30}$ alkyl or $C_3$-$C_{30}$ cycloalkyl, the alkyl or cycloalkyl of the $R^4$ is each independently further substituted with at least one substitute selected from $C_6$-$C_{30}$ aryl and $C_6$-$C_{30}$ heteroaryl, and the heteroaryl includes at least one selected from B, N, O, S, Se, —P(=O)—, —C(=O)—, Si and P.

2. The triazine compound of claim 1, wherein the $R^1$ and $R^2$ are each independently *—NH2 or guanidine; and the $R^4$ is $C_1$-$C_7$ alkyl or $C_3$-$C_7$ cycloalkyl, and the alkyl or cycloalkyl of the $R^4$ is each independently further substituted with at least one substitute selected from $C_6$-$C_{20}$ aryl.

3. The triazine compound of claim 2, wherein the $R^1$ and $R^2$ are each independently *—NH2 or guanidine; and the $R^4$ is $C_{10}$-$C_{20}$ aryl-$C_1$-$C_7$ alkyl or $C_{10}$-$C_{20}$ aryl-$C_3$-$C_7$ cycloalkyl.

4. The triazine compound of claim 1, wherein the triazine compound is at least one selected from following structures:

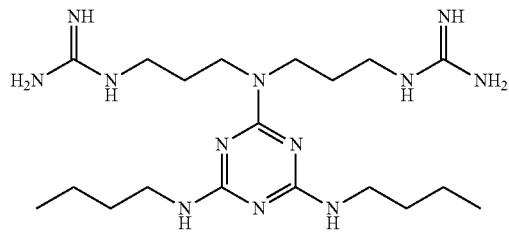

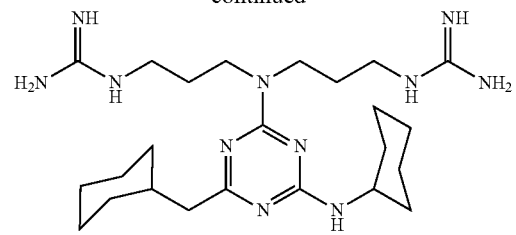

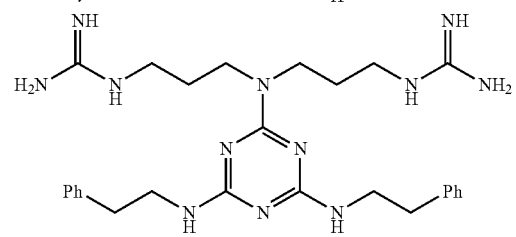

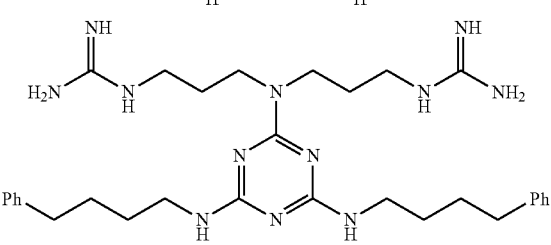

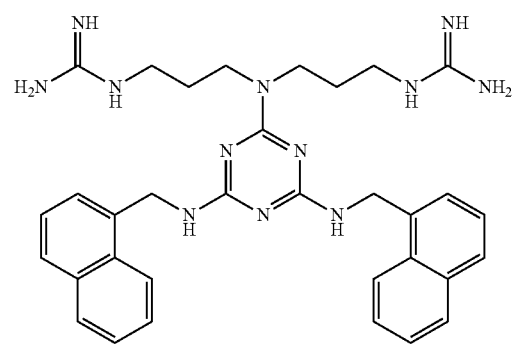

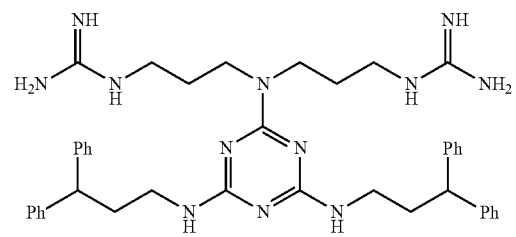

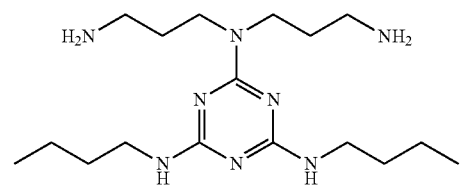

33
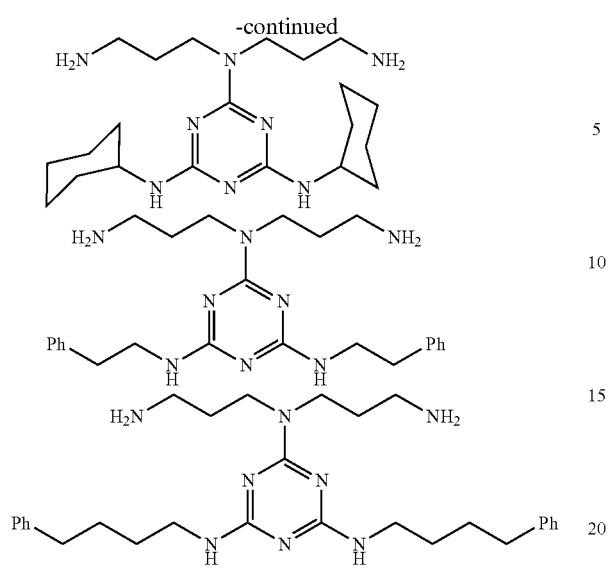
34
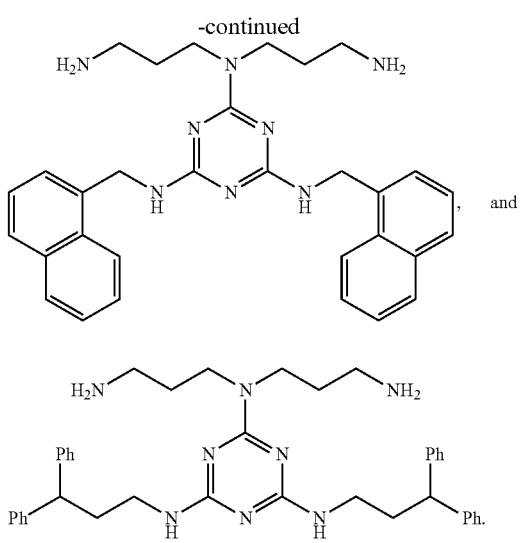
* * * * *